(12) United States Patent
Hlavka et al.

(10) Patent No.: US 7,976,539 B2
(45) Date of Patent: Jul. 12, 2011

(54) SYSTEM AND METHOD FOR DENATURING AND FIXING COLLAGENOUS TISSUE

(75) Inventors: Edwin J. Hlavka, Palo Alto, CA (US);
Frederic H. Moll, Woodside, CA (US);
Robert G. Younge, Portola Valley, CA (US); Daniel T. Wallace, Burlingame, CA (US)

(73) Assignee: Hansen Medical, Inc., Mountain View, CA (US)

( * ) Notice: Subject to any disclaimer, the term of this patent is extended or adjusted under 35 U.S.C. 154(b) by 714 days.

(21) Appl. No.: 11/185,432

(22) Filed: Jul. 19, 2005

(65) Prior Publication Data
US 2006/0057560 A1    Mar. 16, 2006

Related U.S. Application Data

(60) Provisional application No. 60/677,580, filed on May 3, 2005, provisional application No. 60/678,097, filed on May 4, 2005, provisional application No. 60/600,869, filed on Aug. 12, 2004, provisional application No. 60/644,505, filed on Jan. 13, 2005, provisional application No. 60/589,513, filed on Jul. 19, 2004.

(51) Int. Cl.
*A61B 18/04* (2006.01)
(52) U.S. Cl. ............... 606/27; 606/28; 606/41; 128/898
(58) Field of Classification Search ............... 606/27–31, 606/41, 48–50, 213–216
See application file for complete search history.

(56) References Cited

U.S. PATENT DOCUMENTS

| | | | |
|---|---|---|---|
| 3,166,072 A | 1/1965 | Sullivan, Jr. et al. |
| 3,704,711 A | 12/1972 | Park |
| 4,204,283 A | 5/1980 | Bellhouse et al. |
| 4,259,959 A | 4/1981 | Walker |
| 4,492,229 A | 1/1985 | Grunwald |
| 4,524,771 A | 6/1985 | McGregor et al. |
| 4,639,252 A | 1/1987 | Kelly et al. |
| 4,655,773 A | 4/1987 | Grassi |
| 4,731,075 A | 3/1988 | Gallo Mezo et al. |
| 4,816,339 A | 3/1989 | Tu et al. |
| 4,841,888 A | 6/1989 | Mills et al. |
| 4,938,760 A | 7/1990 | Burton et al. |
| 4,945,305 A | 7/1990 | Blood |
| 5,013,316 A | 5/1991 | Goble et al. |
| 5,059,201 A | 10/1991 | Asnis |
| 5,101,592 A | 4/1992 | Merritt |

(Continued)

FOREIGN PATENT DOCUMENTS

DE    10337934    8/2004

(Continued)

OTHER PUBLICATIONS

U.S. Appl. No. 11/073,363, filed Mar. 4, 2005 in the name of Wallace et al., Non-final Office Action mailed Jun. 10, 2009.

(Continued)

*Primary Examiner* — Michael Peffley
(74) *Attorney, Agent, or Firm* — Levine Bagade Han LLP

(57) ABSTRACT

A method for modifying a geometry of a collagenous tissue mass includes heating the collagenous tissue mass to a temperature sufficient to cause denaturation, and introducing a biocompatible fixative, such as genepin, into the collagenous tissue mass.

16 Claims, 36 Drawing Sheets

U.S. PATENT DOCUMENTS

| | | | |
|---|---|---|---|
| 5,108,420 A | 4/1992 | Marks | |
| 5,125,926 A | 6/1992 | Rudko et al. | |
| 5,156,613 A * | 10/1992 | Sawyer | 606/213 |
| 5,171,252 A | 12/1992 | Friedland | |
| 5,222,508 A | 6/1993 | Contarini | |
| 5,224,946 A | 7/1993 | Hayhurst et al. | |
| 5,236,445 A | 8/1993 | Hayhurst et al. | |
| 5,258,016 A | 11/1993 | DiPoto et al. | |
| 5,275,162 A | 1/1994 | Edwards et al. | |
| 5,281,218 A | 1/1994 | Imran | |
| 5,284,488 A | 2/1994 | Sideris | |
| 5,290,300 A | 3/1994 | Cosgrove et al. | |
| 5,304,184 A | 4/1994 | Hathaway et al. | |
| 5,334,217 A | 8/1994 | Das | |
| 5,334,222 A | 8/1994 | Salo et al. | |
| 5,336,252 A | 8/1994 | Cohen | |
| 5,339,799 A | 8/1994 | Kami et al. | |
| 5,354,298 A | 10/1994 | Lee et al. | |
| 5,361,353 A | 11/1994 | Carr et al. | |
| 5,368,015 A | 11/1994 | Wilk | |
| 5,374,275 A | 12/1994 | Bradley et al. | |
| 5,380,334 A | 1/1995 | Torrie et al. | |
| 5,383,897 A | 1/1995 | Wholey | |
| 5,389,076 A | 2/1995 | Shaw et al. | |
| 5,391,199 A | 2/1995 | Ben-Haim | |
| 5,394,875 A | 3/1995 | Lewis et al. | |
| 5,397,443 A | 3/1995 | Michaels | |
| 5,398,691 A | 3/1995 | Martin et al. | |
| 5,403,329 A | 4/1995 | Hinchcliffe | |
| 5,408,409 A | 4/1995 | Glassman et al. | |
| 5,417,699 A | 5/1995 | Klein et al. | |
| 5,423,856 A | 6/1995 | Green | |
| 5,425,744 A | 6/1995 | Fagan et al. | |
| 5,431,666 A | 7/1995 | Sauer et al. | |
| 5,433,727 A | 7/1995 | Sideris | |
| 5,443,446 A | 8/1995 | Shturman | |
| 5,450,860 A | 9/1995 | O'Connor | |
| 5,454,807 A | 10/1995 | Lennox et al. | |
| 5,458,609 A | 10/1995 | Gordon et al. | |
| 5,462,560 A | 10/1995 | Stevens | |
| 5,462,561 A | 10/1995 | Voda | |
| 5,470,338 A | 11/1995 | Whitfield et al. | |
| 5,476,470 A | 12/1995 | Fitzgibbons, Jr. | |
| 5,477,856 A | 12/1995 | Lundquist | |
| 5,480,403 A | 1/1996 | Lee et al. | |
| 5,489,298 A | 2/1996 | Love et al. | |
| 5,489,498 A | 2/1996 | Ohno et al. | |
| 5,492,119 A | 2/1996 | Abrams | |
| 5,492,131 A | 2/1996 | Galel | |
| 5,496,332 A | 3/1996 | Sierra et al. | |
| 5,496,336 A | 3/1996 | Cosgrove et al. | |
| 5,499,991 A | 3/1996 | Garman et al. | |
| 5,501,691 A | 3/1996 | Goldrath | |
| 5,507,744 A * | 4/1996 | Tay et al. | 606/50 |
| 5,507,811 A | 4/1996 | Koike et al. | |
| 5,520,700 A | 5/1996 | Beyar et al. | |
| 5,527,321 A | 6/1996 | Hinchliffe | |
| 5,527,322 A | 6/1996 | Klein et al. | |
| 5,527,342 A | 6/1996 | Pietrzak et al. | |
| 5,540,677 A * | 7/1996 | Sinofsky | 606/8 |
| 5,540,704 A | 7/1996 | Gordon et al. | |
| 5,542,917 A | 8/1996 | Nita et al. | |
| 5,562,686 A | 10/1996 | Sauer et al. | |
| 5,562,688 A | 10/1996 | Riza | |
| 5,571,216 A * | 11/1996 | Anderson | 128/898 |
| 5,578,045 A | 11/1996 | Das | |
| 5,582,616 A | 12/1996 | Bolduc et al. | |
| 5,584,859 A | 12/1996 | Brotz | |
| 5,593,424 A | 1/1997 | Northrup | |
| 5,600,330 A | 2/1997 | Blood | |
| 5,601,558 A | 2/1997 | Torrie et al. | |
| 5,609,598 A | 3/1997 | Laufer et al. | |
| 5,613,974 A | 3/1997 | Andreas et al. | |
| 5,613,975 A | 3/1997 | Christy | |
| 5,631,973 A | 5/1997 | Green | |
| 5,632,752 A | 5/1997 | Buelna | |
| 5,639,276 A | 6/1997 | Weinstock et al. | |
| 5,643,317 A | 7/1997 | Pavcnik et al. | |
| 5,643,320 A | 7/1997 | Lower et al. | |
| 5,662,654 A | 9/1997 | Thompson | |
| 5,662,663 A | 9/1997 | Shallman | |
| 5,662,683 A | 9/1997 | Kay | |
| 5,664,109 A | 9/1997 | Johnson et al. | |
| 5,667,513 A | 9/1997 | Torrie et al. | |
| 5,673,695 A | 10/1997 | McGee et al. | |
| 5,679,005 A | 10/1997 | Einstein | |
| 5,683,402 A | 11/1997 | Cosgrove et al. | |
| 5,690,656 A | 11/1997 | Cope et al. | |
| 5,697,377 A | 12/1997 | Wittkampf | |
| 5,700,273 A | 12/1997 | Buelna et al. | |
| 5,702,421 A | 12/1997 | Schneidt | |
| 5,713,903 A | 2/1998 | Sander et al. | |
| 5,713,946 A | 2/1998 | Ben-Haim | |
| 5,720,753 A | 2/1998 | Sander et al. | |
| 5,722,959 A | 3/1998 | Bierman | |
| 5,724,978 A | 3/1998 | Tenhoff | |
| 5,725,521 A | 3/1998 | Mueller | |
| 5,725,552 A | 3/1998 | Kotula et al. | |
| 5,732,707 A | 3/1998 | Widder et al. | |
| 5,738,096 A | 4/1998 | Ben-Haim | |
| 5,741,297 A | 4/1998 | Simon | |
| 5,749,362 A | 5/1998 | Funda et al. | |
| 5,749,893 A | 5/1998 | Vidal et al. | |
| 5,752,963 A | 5/1998 | Allard et al. | |
| 5,754,741 A | 5/1998 | Wang et al. | |
| 5,762,458 A | 6/1998 | Wang et al. | |
| 5,766,234 A | 6/1998 | Chen et al. | |
| 5,768,578 A | 6/1998 | Kirk et al. | |
| 5,769,846 A | 6/1998 | Edwards et al. | |
| 5,776,189 A | 7/1998 | Khalid | |
| 5,779,719 A | 7/1998 | Klein et al. | |
| 5,784,542 A | 7/1998 | Ohm et al. | |
| 5,792,152 A | 8/1998 | Klein et al. | |
| 5,797,960 A | 8/1998 | Stevens et al. | |
| 5,799,055 A | 8/1998 | Peshkin et al. | |
| 5,810,847 A | 9/1998 | Laufer et al. | |
| 5,810,849 A | 9/1998 | Kontos | |
| 5,814,070 A | 9/1998 | Borzone et al. | |
| 5,815,640 A | 9/1998 | Wang et al. | |
| 5,817,110 A | 10/1998 | Kronner | |
| 5,823,342 A | 10/1998 | Caudillo et al. | |
| 5,823,956 A | 10/1998 | Roth et al. | |
| 5,824,067 A | 10/1998 | Gross | |
| 5,825,982 A | 10/1998 | Wright et al. | |
| 5,827,203 A | 10/1998 | Nita | |
| 5,827,268 A | 10/1998 | Laufer | |
| 5,829,447 A | 11/1998 | Stevens et al. | |
| 5,830,145 A | 11/1998 | Tenhoff | |
| 5,833,608 A | 11/1998 | Acker | |
| 5,836,869 A | 11/1998 | Kudo et al. | |
| 5,836,955 A | 11/1998 | Buelna et al. | |
| 5,843,076 A | 12/1998 | Webster, Jr. et al. | |
| 5,845,646 A | 12/1998 | Lemelson | |
| 5,846,261 A | 12/1998 | Kotula et al. | |
| D404,128 S | 1/1999 | Huebner | |
| 5,855,552 A | 1/1999 | Houser et al. | |
| 5,855,614 A | 1/1999 | Stevens et al. | |
| 5,860,920 A | 1/1999 | McGee et al. | |
| 5,860,991 A | 1/1999 | Klein et al. | |
| 5,861,003 A | 1/1999 | Latson et al. | |
| 5,868,749 A | 2/1999 | Reed | |
| 5,868,762 A | 2/1999 | Cragg et al. | |
| 5,876,325 A | 3/1999 | Mizuno et al. | |
| 5,878,193 A | 3/1999 | Wang et al. | |
| 5,888,247 A | 3/1999 | Benetti | |
| 5,895,404 A | 4/1999 | Ruiz | |
| 5,910,155 A | 6/1999 | Ratcliff et al. | |
| 5,928,224 A | 7/1999 | Laufer | |
| 5,944,738 A | 8/1999 | Amplatz et al. | |
| 5,944,739 A | 8/1999 | Zlock et al. | |
| 5,947,125 A | 9/1999 | Benetti | |
| 5,947,997 A | 9/1999 | Pavcnik et al. | |
| 5,948,000 A | 9/1999 | Larsen et al. | |
| 5,948,001 A | 9/1999 | Larsen | |
| 5,950,629 A | 9/1999 | Taylor et al. | |
| 5,953,683 A | 9/1999 | Hansen et al. | |
| 5,954,732 A | 9/1999 | Hart et al. | |

| | | | |
|---|---|---|---|
| 5,957,916 A | 9/1999 | Jeevanandam et al. | |
| 5,968,047 A | 10/1999 | Reed | |
| 5,972,030 A | 10/1999 | Garrison et al. | |
| 5,983,126 A | 11/1999 | Wittkampf | |
| 5,983,214 A | 11/1999 | Lang et al. | |
| 5,989,284 A | 11/1999 | Laufer | |
| 5,993,459 A | 11/1999 | Larsen et al. | |
| 5,997,534 A | 12/1999 | Tu et al. | |
| 5,997,554 A | 12/1999 | Thompson | |
| 6,004,269 A | 12/1999 | Crowley et al. | |
| 6,004,271 A | 12/1999 | Moore | |
| 6,010,531 A | 1/2000 | Donlon et al. | |
| 6,012,457 A | 1/2000 | Lesh | |
| 6,013,083 A | 1/2000 | Bennett | |
| 6,014,589 A | 1/2000 | Farley et al. | |
| 6,019,768 A | 2/2000 | Wenstrom, Jr. et al. | |
| 6,027,499 A * | 2/2000 | Johnston et al. | 606/22 |
| 6,033,401 A * | 3/2000 | Edwards et al. | 606/41 |
| 6,036,690 A | 3/2000 | De La Plaza Fernandez | |
| 6,052,693 A | 4/2000 | Smith et al. | |
| 6,056,743 A | 5/2000 | Ellis et al. | |
| 6,061,587 A | 5/2000 | Kucharczyk et al. | |
| 6,063,022 A | 5/2000 | Ben-Haim | |
| 6,063,095 A | 5/2000 | Wang et al. | |
| 6,068,648 A | 5/2000 | Cole et al. | |
| 6,074,395 A | 6/2000 | Trott et al. | |
| 6,077,281 A | 6/2000 | Das | |
| 6,077,291 A | 6/2000 | Das | |
| 6,078,924 A | 6/2000 | Ainsbury et al. | |
| 6,079,414 A | 6/2000 | Roth | |
| 6,080,181 A | 6/2000 | Jensen et al. | |
| 6,083,170 A | 7/2000 | Ben-Haim | |
| 6,086,591 A | 7/2000 | Bojarski | |
| 6,086,612 A | 7/2000 | Jansen | |
| 6,096,004 A | 8/2000 | Meglan et al. | |
| 6,096,060 A | 8/2000 | Fitts et al. | |
| 6,098,629 A | 8/2000 | Johnson et al. | |
| 6,106,511 A | 8/2000 | Jensen | |
| 6,113,631 A | 9/2000 | Jansen | |
| 6,120,453 A | 9/2000 | Sharp | |
| 6,123,665 A | 9/2000 | Kawano et al. | |
| 6,126,682 A | 10/2000 | Sharkey et al. | |
| 6,132,368 A | 10/2000 | Cooper | |
| 6,146,387 A | 11/2000 | Trott et al. | |
| 6,149,660 A | 11/2000 | Laufer et al. | |
| 6,151,604 A | 11/2000 | Wlaschin et al. | |
| 6,152,144 A | 11/2000 | Lesh et al. | |
| 6,152,935 A | 11/2000 | Kammerer et al. | |
| 6,159,235 A | 12/2000 | Kim | |
| 6,161,032 A | 12/2000 | Acker | |
| 6,161,543 A | 12/2000 | Cox et al. | |
| 6,163,775 A | 12/2000 | Wlaschin et al. | |
| 6,165,183 A | 12/2000 | Kuehn et al. | |
| 6,167,889 B1 | 1/2001 | Benetti | |
| 6,172,499 B1 | 1/2001 | Ashe | |
| 6,174,287 B1 | 1/2001 | Resnick et al. | |
| 6,187,040 B1 | 2/2001 | Wright | |
| 6,206,886 B1 | 3/2001 | Bennett | |
| 6,226,543 B1 | 5/2001 | Gilboa et al. | |
| 6,228,028 B1 | 5/2001 | Klein et al. | |
| 6,231,561 B1 | 5/2001 | Frazier et al. | |
| 6,233,476 B1 | 5/2001 | Strommer et al. | |
| 6,233,504 B1 | 5/2001 | Das et al. | |
| 6,236,994 B1 | 5/2001 | Swartz et al. | |
| 6,245,079 B1 | 6/2001 | Nobles et al. | |
| 6,246,200 B1 | 6/2001 | Blumenkranz et al. | |
| 6,266,551 B1 | 7/2001 | Osadchy et al. | |
| 6,269,819 B1 | 8/2001 | Oz et al. | |
| 6,270,515 B1 | 8/2001 | Linden et al. | |
| 6,272,371 B1 | 8/2001 | Shlomo | |
| 6,280,448 B1 | 8/2001 | Trott et al. | |
| 6,283,962 B1 | 9/2001 | Tu et al. | |
| 6,283,993 B1 | 9/2001 | Cosgrove et al. | |
| 6,290,674 B1 | 9/2001 | Roue et al. | |
| 6,290,702 B1 | 9/2001 | Fucci et al. | |
| 6,301,496 B1 | 10/2001 | Reisfeld | |
| 6,306,133 B1 | 10/2001 | Tu et al. | |
| 6,309,397 B1 | 10/2001 | Julian et al. | |
| 6,310,828 B1 | 10/2001 | Mumm et al. | |
| 6,311,623 B1 | 11/2001 | Zaruba | |
| 6,312,435 B1 | 11/2001 | Wallace et al. | |
| 6,319,270 B1 | 11/2001 | Grafton et al. | |
| 6,331,181 B1 | 12/2001 | Tierney et al. | |
| 6,332,468 B1 | 12/2001 | Benetti | |
| 6,332,893 B1 | 12/2001 | Mortier et al. | |
| 6,334,873 B1 | 1/2002 | Lane et al. | |
| 6,344,053 B1 | 2/2002 | Boneau | |
| 6,346,074 B1 | 2/2002 | Roth | |
| 6,346,109 B1 | 2/2002 | Fucci et al. | |
| 6,355,030 B1 | 3/2002 | Aldrich et al. | |
| 6,355,052 B1 | 3/2002 | Neuss et al. | |
| 6,363,379 B1 | 3/2002 | Jacobson et al. | |
| 6,363,940 B1 | 4/2002 | Krag | |
| 6,366,921 B1 | 4/2002 | Hansen et al. | |
| 6,368,339 B1 | 4/2002 | Amplatz | |
| 6,370,411 B1 | 4/2002 | Osadchy et al. | |
| 6,371,952 B1 | 4/2002 | Madhani et al. | |
| 6,375,471 B1 | 4/2002 | Wendlandt et al. | |
| 6,380,732 B1 | 4/2002 | Gilboa | |
| 6,381,483 B1 | 4/2002 | Hareyama et al. | |
| 6,393,340 B2 | 5/2002 | Funda et al. | |
| 6,398,731 B1 | 6/2002 | Mumm et al. | |
| 6,400,979 B1 | 6/2002 | Stoianovici et al. | |
| 6,409,759 B1 | 6/2002 | Peredo | |
| 6,415,171 B1 | 7/2002 | Gueziec et al. | |
| 6,424,885 B1 | 7/2002 | Niemeyer et al. | |
| 6,440,154 B2 | 8/2002 | Gellman et al. | |
| 6,451,024 B1 | 9/2002 | Thompson et al. | |
| 6,468,265 B1 | 10/2002 | Evans et al. | |
| 6,472,983 B1 | 10/2002 | Grunder | |
| 6,491,701 B2 | 12/2002 | Tierney et al. | |
| 6,493,573 B1 | 12/2002 | Martinelli et al. | |
| 6,493,608 B1 | 12/2002 | Niemeyer | |
| 6,530,913 B1 | 3/2003 | Giba et al. | |
| 6,544,230 B1 | 4/2003 | Flaherty et al. | |
| 6,547,787 B1 | 4/2003 | Altman et al. | |
| 6,551,273 B1 | 4/2003 | Olson et al. | |
| 6,564,215 B1 | 5/2003 | Hsiao et al. | |
| 6,565,554 B1 | 5/2003 | Niemeyer | |
| 6,574,355 B2 | 6/2003 | Green | |
| 6,580,938 B1 | 6/2003 | Acker | |
| 6,583,117 B2 * | 6/2003 | Owen et al. | 514/12 |
| 6,587,750 B2 | 7/2003 | Gerbi et al. | |
| 6,592,610 B2 | 7/2003 | Beyar | |
| 6,594,552 B1 | 7/2003 | Nowlin et al. | |
| 6,599,310 B2 | 7/2003 | Leung et al. | |
| 6,610,007 B2 | 8/2003 | Belson et al. | |
| 6,615,155 B2 | 9/2003 | Gilboa | |
| 6,616,684 B1 | 9/2003 | Vidlund et al. | |
| 6,618,612 B1 | 9/2003 | Acker et al. | |
| 6,619,291 B2 | 9/2003 | Hlavka et al. | |
| 6,620,173 B2 | 9/2003 | Gerbi et al. | |
| 6,622,731 B2 * | 9/2003 | Daniel et al. | 128/898 |
| 6,626,899 B2 | 9/2003 | Houser et al. | |
| 6,629,097 B1 | 9/2003 | Keith | |
| 6,629,534 B1 | 10/2003 | St. Goar et al. | |
| 6,643,661 B2 | 11/2003 | Polizzi et al. | |
| 6,659,939 B2 | 12/2003 | Moll et al. | |
| 6,669,687 B1 | 12/2003 | Saadat | |
| 6,669,709 B1 | 12/2003 | Cohn et al. | |
| 6,673,041 B1 | 1/2004 | Macoviak | |
| 6,685,698 B2 | 2/2004 | Morley et al. | |
| 6,694,307 B2 | 2/2004 | Julien | |
| 6,695,866 B1 | 2/2004 | Kuehn et al. | |
| 6,699,235 B2 | 3/2004 | Wallace et al. | |
| 6,702,826 B2 | 3/2004 | Liddicoat et al. | |
| 6,716,166 B2 | 4/2004 | Govari | |
| 6,718,985 B2 | 4/2004 | Hlavka et al. | |
| 6,719,785 B2 | 4/2004 | Schoon et al. | |
| 6,726,675 B1 | 4/2004 | Beyar | |
| 6,733,458 B1 | 5/2004 | Steins et al. | |
| 6,735,578 B2 | 5/2004 | Shetty et al. | |
| 6,740,107 B2 | 5/2004 | Loeb et al. | |
| 6,743,239 B1 | 6/2004 | Kuehn et al. | |
| 6,743,248 B2 * | 6/2004 | Edwards et al. | 606/214 |
| 6,746,472 B2 | 6/2004 | Frazier et al. | |
| 6,774,624 B2 | 8/2004 | Anderson et al. | |
| 6,783,524 B2 | 8/2004 | Anderson et al. | |

| | | |
|---|---|---|
| 6,796,963 B2 | 9/2004 | Carpenter et al. |
| 6,799,065 B1 | 9/2004 | Niemeyer |
| 6,817,973 B2 | 11/2004 | Merril et al. |
| 6,817,974 B2 | 11/2004 | Cooper et al. |
| 6,835,193 B2 | 12/2004 | Epstein et al. |
| 6,852,107 B2 | 2/2005 | Wang et al. |
| 6,858,003 B2 | 2/2005 | Evans et al. |
| 6,862,585 B2 | 3/2005 | Planalp et al. |
| 6,886,010 B2 | 4/2005 | Kostoff |
| 6,905,460 B2 | 6/2005 | Wang et al. |
| 6,911,019 B2 | 6/2005 | Mulier et al. |
| 6,963,792 B1 | 11/2005 | Green |
| 7,021,173 B2 | 4/2006 | Stoianovici et al. |
| 7,074,179 B2 | 7/2006 | Wang et al. |
| 7,087,049 B2 | 8/2006 | Nowlin et al. |
| 7,087,064 B1 | 8/2006 | Hyde |
| 7,101,395 B2 | 9/2006 | Tremulis et al. |
| 7,101,857 B2 * | 9/2006 | Sung et al. ................... 514/26 |
| 7,169,141 B2 | 1/2007 | Brock et al. |
| 7,186,262 B2 | 3/2007 | Saadat |
| 7,189,199 B2 | 3/2007 | McCarthy et al. |
| 7,217,284 B2 | 5/2007 | Houser et al. |
| 7,225,012 B1 | 5/2007 | Susil et al. |
| 7,297,142 B2 | 11/2007 | Brock |
| 7,320,700 B2 | 1/2008 | Cooper et al. |
| 7,331,967 B2 | 2/2008 | Lee et al. |
| 7,343,195 B2 | 3/2008 | Strommer et al. |
| 7,371,210 B2 | 5/2008 | Brock et al. |
| 7,404,824 B1 | 7/2008 | Webler et al. |
| 7,494,494 B2 | 2/2009 | Stoianovici et al. |
| 7,562,660 B2 | 7/2009 | Saadat |
| 7,632,308 B2 | 12/2009 | Loulmet |
| 7,699,805 B2 | 4/2010 | Mulier et al. |
| 7,753,924 B2 | 7/2010 | Starksen et al. |
| 2001/0009976 A1 | 7/2001 | Panescu et al. |
| 2001/0029366 A1 | 10/2001 | Swanson et al. |
| 2002/0035361 A1 | 3/2002 | Houser et al. |
| 2002/0065857 A1 | 5/2002 | Michalewicz et al. |
| 2002/0078068 A1 | 6/2002 | Krishnaprasad et al. |
| 2002/0087048 A1 | 7/2002 | Brock et al. |
| 2002/0087049 A1 | 7/2002 | Brock et al. |
| 2002/0087166 A1 | 7/2002 | Brock et al. |
| 2002/0087169 A1 | 7/2002 | Brock et al. |
| 2002/0095167 A1 | 7/2002 | Liddicoat et al. |
| 2002/0095175 A1 | 7/2002 | Brock et al. |
| 2002/0128997 A1 | 9/2002 | Kil et al. |
| 2002/0128998 A1 | 9/2002 | Kil et al. |
| 2002/0138009 A1 | 9/2002 | Brockway et al. |
| 2002/0152208 A1 | 10/2002 | Bloedorn |
| 2002/0156771 A1 | 10/2002 | Frieder et al. |
| 2002/0161378 A1 | 10/2002 | Downing |
| 2002/0161626 A1 | 10/2002 | Plante et al. |
| 2002/0177789 A1 | 11/2002 | Ferry et al. |
| 2002/0194379 A1 | 12/2002 | Bennett et al. |
| 2003/0014010 A1 | 1/2003 | Carpenter |
| 2003/0014406 A1 | 1/2003 | Faieta et al. |
| 2003/0018358 A1 | 1/2003 | Saadat |
| 2003/0033275 A1 | 2/2003 | Alpha et al. |
| 2003/0073908 A1 | 4/2003 | Desai |
| 2003/0074011 A1 | 4/2003 | Gilboa et al. |
| 2003/0078465 A1 | 4/2003 | Pai et al. |
| 2003/0083908 A1 | 5/2003 | Steinmann |
| 2003/0088562 A1 | 5/2003 | Dillon et al. |
| 2003/0105519 A1 | 6/2003 | Fasol et al. |
| 2003/0105520 A1 | 6/2003 | Alferness et al. |
| 2003/0109780 A1 | 6/2003 | Coste-Maniere et al. |
| 2003/0120133 A1 | 6/2003 | Rao et al. |
| 2003/0120134 A1 | 6/2003 | Rao et al. |
| 2003/0125988 A1 | 7/2003 | Rao et al. |
| 2003/0130894 A1 | 7/2003 | Huettner et al. |
| 2003/0135204 A1 | 7/2003 | Lee et al. |
| 2003/0149375 A1 | 8/2003 | Chen et al. |
| 2003/0149586 A1 | 8/2003 | Chen et al. |
| 2003/0149730 A1 | 8/2003 | Kumar et al. |
| 2003/0158865 A1 | 8/2003 | Renkes et al. |
| 2003/0176976 A1 | 9/2003 | Gardner |
| 2003/0177112 A1 | 9/2003 | Gardner |
| 2003/0177143 A1 | 9/2003 | Gardner |
| 2003/0204494 A1 | 10/2003 | Agrawal et al. |
| 2003/0225749 A1 | 12/2003 | Cox et al. |
| 2003/0233142 A1 | 12/2003 | Morales et al. |
| 2004/0010491 A1 | 1/2004 | Riedinger |
| 2004/0019378 A1 | 1/2004 | Hlavka et al. |
| 2004/0024414 A1 | 2/2004 | Downing |
| 2004/0034282 A1 | 2/2004 | Quaid |
| 2004/0034365 A1 | 2/2004 | Lentz et al. |
| 2004/0044659 A1 | 3/2004 | Judd et al. |
| 2004/0049473 A1 | 3/2004 | Gower et al. |
| 2004/0049505 A1 | 3/2004 | Pennock |
| 2004/0103116 A1 | 5/2004 | Palanisamy et al. |
| 2004/0111302 A1 | 6/2004 | Falk et al. |
| 2004/0133192 A1 | 7/2004 | Houser et al. |
| 2004/0152947 A1 | 8/2004 | Schroeder et al. |
| 2004/0167870 A1 | 8/2004 | Wakefield et al. |
| 2004/0167883 A1 | 8/2004 | Wakefield et al. |
| 2004/0167884 A1 | 8/2004 | Wakefield et al. |
| 2004/0167885 A1 | 8/2004 | Wakefield et al. |
| 2004/0167886 A1 | 8/2004 | Wakefield et al. |
| 2004/0167887 A1 | 8/2004 | Wakefield et al. |
| 2004/0167907 A1 | 8/2004 | Wakefield et al. |
| 2004/0167908 A1 | 8/2004 | Wakefield et al. |
| 2004/0167909 A1 | 8/2004 | Wakefield et al. |
| 2004/0167910 A1 | 8/2004 | Wakefield et al. |
| 2004/0167911 A1 | 8/2004 | Wakefield et al. |
| 2004/0172297 A1 | 9/2004 | Rao et al. |
| 2004/0176751 A1 | 9/2004 | Weitzner et al. |
| 2004/0186826 A1 | 9/2004 | Choi et al. |
| 2004/0193146 A1 | 9/2004 | Lee et al. |
| 2004/0225653 A1 | 11/2004 | Nelken et al. |
| 2004/0243554 A1 | 12/2004 | Broder et al. |
| 2004/0243645 A1 | 12/2004 | Broder et al. |
| 2005/0004909 A1 | 1/2005 | Stevenson et al. |
| 2005/0010454 A1 | 1/2005 | Falk et al. |
| 2005/0038805 A1 | 2/2005 | Maren et al. |
| 2005/0049497 A1 | 3/2005 | Krishnan et al. |
| 2005/0050037 A1 | 3/2005 | Frieder et al. |
| 2005/0055355 A1 | 3/2005 | Murthy et al. |
| 2005/0059876 A1 | 3/2005 | Krishnan et al. |
| 2005/0059960 A1 | 3/2005 | Simaan et al. |
| 2005/0065807 A1 | 3/2005 | DeAngelis et al. |
| 2005/0065941 A1 | 3/2005 | DeAngelis et al. |
| 2005/0065967 A1 | 3/2005 | Schuetze et al. |
| 2005/0075723 A1 | 4/2005 | Schroeder et al. |
| 2005/0086215 A1 | 4/2005 | Perisic |
| 2005/0086222 A1 | 4/2005 | Wang et al. |
| 2005/0091285 A1 | 4/2005 | Krishnan et al. |
| 2005/0107688 A1 | 5/2005 | Strommer |
| 2005/0108256 A1 | 5/2005 | Wakefield et al. |
| 2005/0108267 A1 | 5/2005 | Gibson et al. |
| 2005/0131460 A1 | 6/2005 | Gifford, III et al. |
| 2005/0159789 A1 | 7/2005 | Brockway et al. |
| 2005/0165276 A1 | 7/2005 | Belson et al. |
| 2005/0182295 A1 | 8/2005 | Soper et al. |
| 2005/0182330 A1 | 8/2005 | Brockway et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0200324 A1 | 9/2005 | Guthart et al. |
| 2005/0203382 A1 | 9/2005 | Govari et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0222554 A1 | 10/2005 | Wallace et al. |
| 2006/0009802 A1 * | 1/2006 | Modesitt ................... 606/215 |
| 2006/0013523 A1 | 1/2006 | Childers et al. |
| 2006/0058647 A1 | 3/2006 | Strommer et al. |
| 2006/0064006 A1 | 3/2006 | Strommer et al. |
| 2006/0084945 A1 * | 4/2006 | Moll et al. ................... 606/1 |
| 2006/0111692 A1 | 5/2006 | Hlavka et al. |
| 2006/0178556 A1 | 8/2006 | Hasser et al. |
| 2006/0200049 A1 | 9/2006 | Leo et al. |
| 2006/0258938 A1 | 11/2006 | Hoffman et al. |
| 2006/0271036 A1 | 11/2006 | Garabedian et al. |
| 2006/0287661 A1 | 12/2006 | Bolduc et al. |
| 2006/0287716 A1 | 12/2006 | Banbury et al. |
| 2006/0293643 A1 | 12/2006 | Wallace et al. |
| 2007/0038181 A1 | 2/2007 | Melamud et al. |
| 2007/0060847 A1 | 3/2007 | Leo et al. |

| | | | |
|---|---|---|---|
| 2007/0060879 | A1 | 3/2007 | Weitzner et al. |
| 2007/0065077 | A1 | 3/2007 | Childers et al. |
| 2007/0073387 | A1 | 3/2007 | Forster et al. |
| 2007/0118154 | A1 | 5/2007 | Crabtree |
| 2007/0123851 | A1 | 5/2007 | Alejandro et al. |
| 2007/0129758 | A1 | 6/2007 | Saadat |
| 2007/0203560 | A1 | 8/2007 | Forster et al. |
| 2007/0203561 | A1 | 8/2007 | Forster et al. |
| 2007/0203575 | A1 | 8/2007 | Forster et al. |
| 2007/0208357 | A1 | 9/2007 | Houser et al. |
| 2007/0287999 | A1 | 12/2007 | Malecki et al. |
| 2007/0293724 | A1 | 12/2007 | Saadat et al. |
| 2007/0299434 | A1 | 12/2007 | Malecki et al. |
| 2008/0009746 | A1 | 1/2008 | Forster et al. |
| 2008/0009750 | A1 | 1/2008 | Aeby et al. |
| 2008/0015445 | A1 | 1/2008 | Saadat et al. |
| 2008/0300592 | A1 | 12/2008 | Weitzner et al. |
| 2009/0054884 | A1 | 2/2009 | Farley et al. |
| 2009/0182224 | A1 | 7/2009 | Shmarak et al. |
| 2009/0264994 | A1 | 10/2009 | Saadat |
| 2010/0049311 | A1 | 2/2010 | Loulmet |

FOREIGN PATENT DOCUMENTS

| | | |
|---|---|---|
| EP | 1083491 | 3/2001 |
| JP | 1021249 | 1/1989 |
| JP | 2004258912 | 9/2004 |
| WO | WO 90/09763 | 9/1990 |
| WO | WO 92/17118 | 10/1992 |
| WO | WO 96/30845 | 3/1996 |
| WO | WO 97/32532 | 9/1997 |
| WO | WO 97/44089 | 11/1997 |
| WO | WO 98/32401 | 7/1998 |
| WO | WO 98/35469 | 8/1998 |
| WO | WO 98/35638 | 8/1998 |
| WO | WO 98/38936 | 9/1998 |
| WO | WO 99/02096 | 1/1999 |
| WO | WO 99/05983 | 2/1999 |
| WO | WO 00/11495 | 2/2000 |
| WO | WO 00/45193 | 3/2000 |
| WO | WO 00/60995 | 10/2000 |
| WO | WO 00/27292 | 11/2000 |
| WO | WO 01/00114 | 1/2001 |
| WO | WO 01/26557 | 4/2001 |
| WO | WO 01/28432 | 4/2001 |
| WO | WO 02/065933 | 8/2002 |
| WO | WO 02/095616 | 11/2002 |
| WO | WO 03/003930 | 1/2003 |
| WO | WO 03/040878 | 5/2003 |
| WO | WO 03/040892 | 5/2003 |
| WO | WO 03/091839 | 6/2003 |
| WO | WO 03/077769 | 9/2003 |
| WO | WO 03/098466 | 11/2003 |
| WO | WO 03/105670 | 12/2003 |
| WO | WO 2004/104865 | 2/2004 |
| WO | WO 2005/102181 | 11/2005 |
| WO | WO 2007/061834 | 5/2007 |

OTHER PUBLICATIONS

U.S. Appl. No. 11/073,363, filed Mar. 4, 2005 in the name of Wallace et al., Final Office Action mailed Jan. 21, 2010.
PCT International Search Report for PCT/US2005/007108, Applicant Hansen Medical, Inc., Forms PCTIISAI210 and 220, dated Jun. 26, 2005 (9 pages).
PCT Written Opinion of the International Search Authority for PCT/US2005/007108, Applicant Hansen Medical, Inc., Form PCT/ISAI237, dated Jun. 26, 2005 (6 pages).
"Adding Structure to the Unstructured-Computer Business Review,", http://www.cbr-online.com, World Wide Web, May 25, 2005, pp. 1-6.
Alfred Z. Spector, "Architecting Knowledge Middleware;" http://itlab.uta.edu/idm01/FinalReports/Innovation.pdf, World Wide Web, 2002. pp, 1-40.
Aaron Zornes, "EA Community Articles", http://www.eacommunity.com/articles/openarticle.asp?ID=1834>, World Wide Web, May 25, 2005, pp. 1-3.
Beth Gold-Bernstein, "EbizQ Integration Conference", http://www.ebizq.net/topics/portals/features/4371.html?page=2&pp=I >, World Wide Web, May 10, 2005, pp. 1-5.

"EIQ Server", http://www.whamtech.com/eiq_server.htm>, World Wide Web, May 25, 2005, pp. 1-3.
Stephen Swoyer, "IBM's BI Middleware Play: Its All About Integration, Partnerships", http://www.tdwi.org/Publications/display.aspx?id+7267&t=y, World Wide Web, Nov. 3, 2004, pp. 1-3.
Barbara Darrow, "IBM Looks to 'Viper' Database to Combat Oracle, Microsoft", http://www.bizintellignecepipeline.com/shared/article/printable.ArticleSrc.Jhtml, World Wide Web, May 25, 2005, pp. 1-5.
Infoconomy Staff, "Enterprise Search Tools", http://www.infoconomy.com/pages/infoconomist-crib-sheets/group101866.adp, World Wide Web, Dec. 1, 2004, pp. 1-5.
Min Wang et. al., "Database Research at Watson", http://www.research.ibm.com/scalabledb/semistruct.html, World Wide Web, May 25, 2005, pp. 1-3.
"Innovative Applications;", http://www2002.org/spector.pdg, World Wide Web, pp. 1-5.
D. Ferrucci, "Building An Example Application With The Unstructured Information Management Architecture", http://www.findarticles.com/p/articles/mi_mlSJ/is_3_43/ai_n7576557/print, World Wide Web, Mar. 16, 2004, pp. 1-22.
Robert Bourret, "Persistence: SGML and XML in Databases", http://www.isgmlug.org/database.html, World Wide Web, 2002, pp. 1-5.
Robert D. Kugel, "Transform Magazine: Unstructured Information Management", http://www.transformmag.com/shard/cp/print_article.jthml:sessionid. >, World Wide Web, Dec. 2003, pp. 1-3.
"The Unstructured Information Management Architecture Project", http://www.research.ibm.com/UIMA/>, World Wide Web, May 25, 2005, pp. 1-2.
European Patent Application No. 00944803.6 filed Jun. 23, 2000 in the name of Saadat et al., Communication under Rule 71(3) mailed Nov. 20, 2009.
European Patent Application No. 00944803.6 filed Jun. 23, 2000 in the name of Saadat et al., office action mailed Aug. 8, 2008.
European Patent Application No. 00944803.6 filed Jun. 23, 2000 in the name of Saadat et al., office action mailed Mar. 16, 2009.
European Patent Application No. 00944803.6 filed Jun. 23, 2000 in the name of Saadat et al., Search Report mailed Jun. 3, 2005.
European Patent Application No. 02749755.1 filed Jul. 3, 2002 in the name of Houser et al., Search Report mailed Sep. 16, 2009.
Hayashi, K. et al. (1997). "The Effect of Thermal Heating on the Length and Histologic Properties of the Glenohumeral Joint Capsule", *The American Journal of Sports Medicine*, 25(1): 107-112.
Japanese Patent Application No. 2001-505831 filed Jun. 23, 2000 in the name of Saadat et al., Notice of Allowance mailed Jun. 29, 2010.
Japanese Patent Application No. 2001-505831 filed Jun. 23, 2000 in the name of Saadat et al., office action mailed Jan. 12, 2010.
Naseef III, G. S. etal. (1997). "The Thermal Properties of Bovine Joint Capsule, The Basic Science of Laser-and Radiofrequency-Induced Capsular Shrinkage", *The American Journal of Sports Medicine*, 25(5):670-674.
PCT Patent Application No. PCT/US2000/017270 filed Jun. 23. 2000 in the name of Saadat, Search Report mailed Oct. 12, 2000.
PCT Patent Application No. PCT/US2002/020996 filed Jul. 3, 2002 in the name of Houser et al., Search Report mailed Sep. 19, 2002.
PCT Patent Application No. PCT/US2005/028877 filed Aug. 12, 2005 in the name of Moll et al., Search Report and Written Opinion mailed Nov. 22, 2005.
PCT Patent Application No. PCT/US2006/044655 filed Nov. 15, 2006 in the name of Loulmet, Search Report and Written Opinion mailed May 1, 2007.
Penny Lunt Lunt Crosman, "Content Pipeline", http://messagingpipeline.com/shared/article/printableArticleSrc.jhtml?articleId=51201811>, World Wide Web, Nov. 1, 2004, pp. 1-8.
Selecky, M. T. et al. (1996). "The Effects of Laser-Induced Collagen Shortening on the Biomechanical Properties of the Inferior Glenohumeral Ligament Complex", Univety of Southern California, School of Medicine, Department of Orthopaedic Surgery, Los Angeles, California, 90033, pp. 1-25.
U.S. Appl. No. 09/602,436 filed Jun. 23, 2000 in the name of Saadat, non-final Office Action mailed Jan. 29, 2003.
U.S. Appl. No. 09/602,436 filed Jun. 23, 2000 in the name of Saadat, non-final Office Action mailed Jul. 16, 2002.

U.S. Appl. No. 09/602,436 filed Jun. 23, 2000 in the name of Saadat, non-final Office Action mailed Mar. 29, 2002.
U.S. Appl. No. 09/602,436 filed Jun. 23, 2000 in the name of Saadat, Notice of Allowance mailed Sep. 12, 2003.
U.S. Appl. No. 09/898,726 filed Jul. 3, 2001 in the name of Houser et al., final Office Action mailed Feb. 26, 2003.
U.S. Appl. No. 09/898,726 filed Jul. 3, 2001 in the name of Houser et al., non-final Office Action mailed Sep. 25, 2002.
U.S. Appl. No. 09/898,726 filed Jul. 3, 2001 in the name of Houser et al., Notice of Allowance mailed Jun. 2, 2003.
U.S. Appl. No. 10/188,509 filed Jul. 3, 2002 in the name of Saadat, final Office Action mailed Mar. 3, 2006.
U.S. Appl. No. 10/188,509 filed Jul. 3, 2002 in the name of Saadat, non-final Office Action mailed Feb. 12, 2004.
U.S. Appl. No. 10/188,509 filed Jul. 3, 2002 in the name of Saadat, non-final Office Action mailed Jul. 27, 2005.
U.S. Appl. No. 10/188,509 filed Jul. 3, 2002 in the name of Saadat, non-final Office Action mailed Nov. 5, 2004.
U.S. Appl. No. 10/188,509 filed Jul. 3, 2002 in the name of Saadat, Notice of Allowance mailed Sep. 19, 2006.
U.S. Appl. No. 10/669,204 filed Sep. 23, 2003 in the name of Houser et al., final Office Action mailed Feb. 9, 2005.
U.S. Appl. No. 10/669,204 filed Sep. 23, 2003 in the name of Houser et al., final Office Action mailed Jul. 14, 2006.
U.S. Appl. No. 10/669,204 filed Sep. 23, 2003 in the name of Houser et al., non-final Office Action mailed May 18, 2004.
U.S. Appl. No. 10/669,204 filed Sep. 23, 2003 in the name of Houser et al., non-final Office Action mailed Nov. 22, 2005.
U.S. Appl. No. 10/669,204 filed Sep. 23, 2003 in the name of Houser et al., Notice of Allowance mailed Jan. 8, 2007.
U.S. Appl. No. 11/073,363 filed Mar. 4, 2005 in the name of Wallace et al., Non-final Office Action mailed Jun. 8, 2010.
U.S. Appl. No. 11/176,957 filed Jul. 6, 2005 in the name of Wallace et al., Final Office Action mailed Oct. 26, 2010.
U.S. Appl. No. 11/176,957 filed Jul. 6, 2005 in the name of Wallace et al., Non-final Office Action mailed May 10, 2010.
U.S. Appl. No. 11/202,925 filed Aug. 12, 2005 in the name of Hlavka et al., final Office Action mailed Oct. 27, 2010.
U.S. Appl. No. 11/202,925 filed Aug. 12, 2005 in the name of Hlavka et al., non-final Office Action mailed May 11, 2010.
U.S. Appl. No. 11/286,037 filed Nov. 23, 2005 in the name of Loulmet, non-final Office Action mailed Jan. 15, 2009.
U.S. Appl. No. 11/286,037 filed Nov. 23, 2005 in the name of Loulmet, Notice of Allowance mailed Sep. 17, 2009.
U.S. Appl. No. 11/622,442 filed Jan. 11, 2007 in the name of Saadat, Non-final Office Action mailed Jun. 25, 2008.
U.S. Appl. No. 11/622,442 filed Jan. 11, 2007 in the name of Saadat, Notice of Allowance mailed Mar. 23, 2009.
U.S. Appl. No. 11/743,343 filed May 2, 2007 in the name of Houser et al., Final Office Action mailed May 5, 2010.
U.S. Appl. No. 11/743,343 filed May 2, 2007 in the name of Houser et al., non-final Office Action mailed Jul. 21, 2009.
U.S. Appl. No. 12/608,849 filed Oct. 29, 2009 in the name of Loulmet, non-final Office Action mailed Jun. 24, 2010, 2010.
European Patent Application No. 02749755.1 filed Jul. 3, 2002 in the name of Houser et al., Office Action mailed Dec. 16, 2009.
European Patent Application No. 02749755.1 filed Jul. 3, 2002 in the name of Houser et al., Office Action mailed Mar. 1, 2011.
U.S. Appl. No. 11/073,363 filed Mar. 4, 2005 in the name of Wallace et al., Final Office Action mailed Dec. 21, 2010.
U.S. Appl. No. 11/073,363 filed Mar. 4, 2005 in the name of Wallace et al., Notice of Allowance mailed Mar. 10, 2011.
U.S. Appl. No. 11/176,957 filed Jul. 6, 2005 in the name of Wallace et al., Notice of Allowance mailed Mar. 17, 2011.
U.S. Appl. No. 11/202,925 filed Aug. 12, 2005 in the name of Hlavka et al., Notice of Allowance mailed Apr. 12, 2011.
U.S. Appl. No. 12/608,849 filed Oct. 29, 2009 in the name of Loulmet, Final Office Action mailed Mar. 23, 2011.
U.S. Appl. No. 12/489,258 filed Jun. 22, 2009 in the name of Saadat, Non-Final Office Action mailed Feb. 15, 2011.

* cited by examiner

341 ⟶

O═CH—CH₂—CH₂—CH₂—CH═O

Glutaraldehyde

Genipin

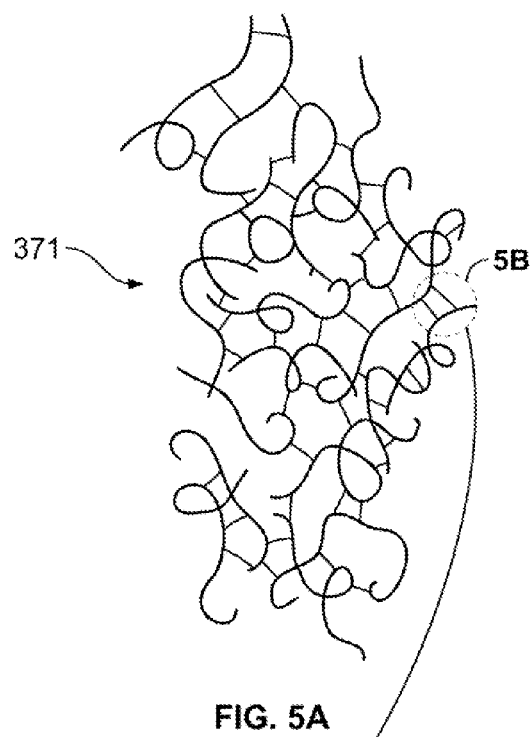
FIG. 5A
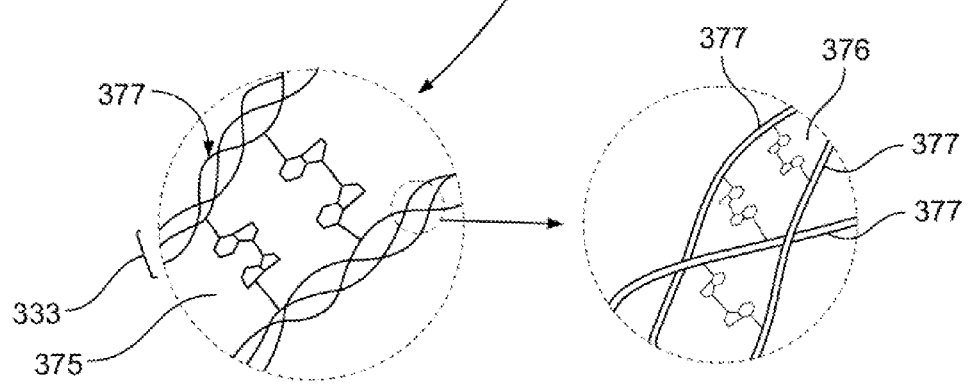
FIG. 5B
FIG. 5C

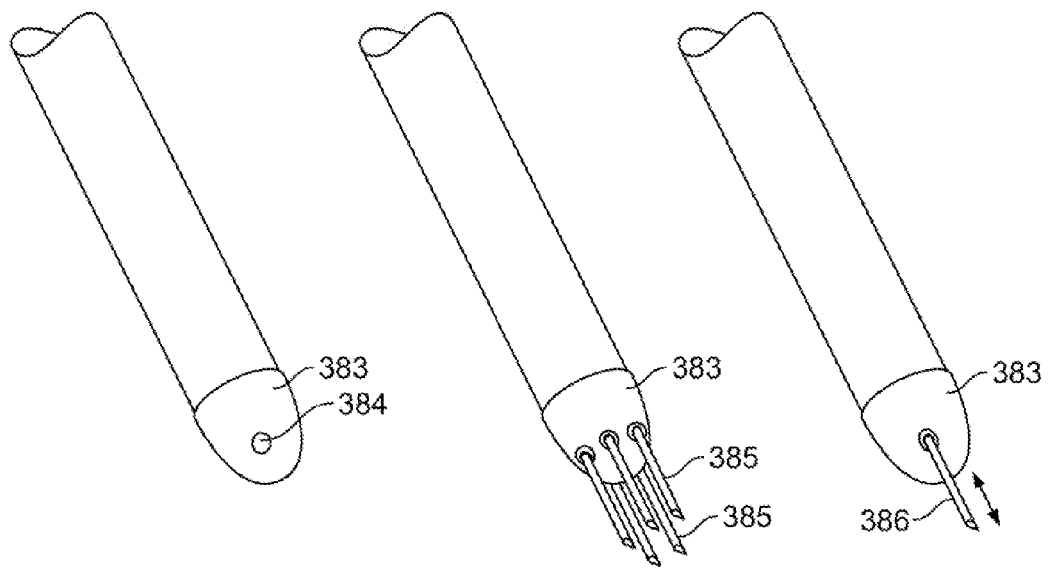
FIG. 11A  FIG. 11B  FIG. 11C
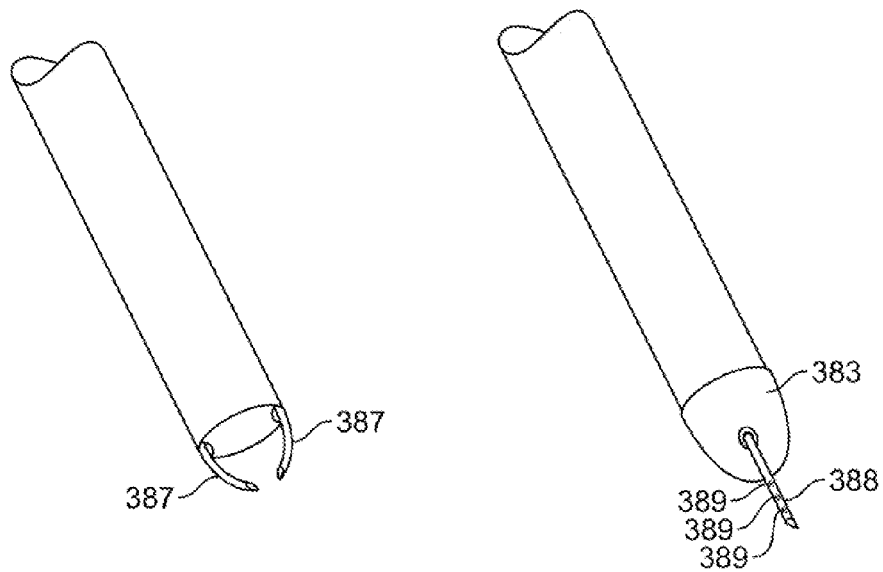
FIG. 11D  FIG. 11E

SYSTEM AND METHOD FOR DENATURING AND FIXING COLLAGENOUS TISSUE

RELATED APPLICATION DATA

The present application claims the benefit under 35 U.S.C. §119 to U.S. provisional patent application Ser. Nos. 60/677,580, filed May 3, 2005, and 60/678,097, filed May 4, 2005, 60/600,869, filed Aug. 12, 2004, 60/644,505, filed Jan. 13, 2005 and 60/589,513, filed Jul. 19, 2004. The foregoing applications, along with U.S. patent application Ser. No. 11/176,957, filed Jul. 6, 2005, and Ser. No. 11/073,363, filed Mar. 4, 2005, are hereby incorporated by reference into the present application in their entirety.

FIELD OF INVENTION

The invention relates generally to catheter-based systems and method for treating tissue using controlled denaturation of collagen.

BACKGROUND

Referring to FIG. 1A, a collagenous tissue mass (327) is depicted. Collagen is one of the fundamental building blocks of the soft tissues of the human body. A collagenous tissue mass (327) typically comprises groupings of collagen fibrils (328) which are mechanically associated with each other by crosslinks (329), as depicted in the close-up view of FIG. 1B. Cross links (329) stiffen the overall mechanical properties of the tissue mass (327). Also shown in the close-up view of FIG. 1B is the triple helix structure (331) that typically comprises each of the collagen fibrils (328). As collagenous tissue is heated above about 60 degrees C., and thereby at least partially denatured, crosslinking bonds contributing to the mechanical and geometric association of the fibrils begin to break down, and normally linearly stretched out fibrils tend to recoil. Referring to FIG. 2A, a denatured collagenous tissue mass (335) is depicted comprising at least partially recoiled collagen fibrils (333) and some broken crosslinks (337) between previously coupled fibrils. The result of this transformation is a net overall reduction in geometry (339) of the denatured collagenous tissue mass (335). Along with this geometric change, the mechanical properties of the tissue mass change. The tissue may become weaker and more susceptible to creep deformation as it is loaded over time. Creep deformation under load can essentially reverse geometric gains achieved with procedures aimed at locally modifying tissue with collagen denaturation. In orthopaedic settings, for example, RF-based localized denaturation accomplished using devices from providers such as Oratec Interventions, Inc. and DePuy-Mitek, a Johnson & Johnson company, has been shown to be at least partially effective in the short term for tightening lax ligaments, but subsequent to loading over time, some ligament laxity may return, thereby decreasing the long-term effectiveness of the procedure. To address this challenge in such applications, immobilization and unloading of the targeted tissue may be a partial solution, but this solution also has well-known downsides. In summary, there is a heed for a solution to at least partially recover the properties of denatured collagenous tissue subsequent to denaturation treatment for geometric modification.

BRIEF DESCRIPTION OF THE DRAWINGS

FIGS. 5A-5C shows a denatured collagenous tissue mass after being exposed to Genepin.
FIGS. 11A-H shows various hybrid distal tip structures for an elongate instrument.

DETAILED DESCRIPTION OF THE ILLUSTRATED EMBODIMENTS

Figures 1A, 1B:
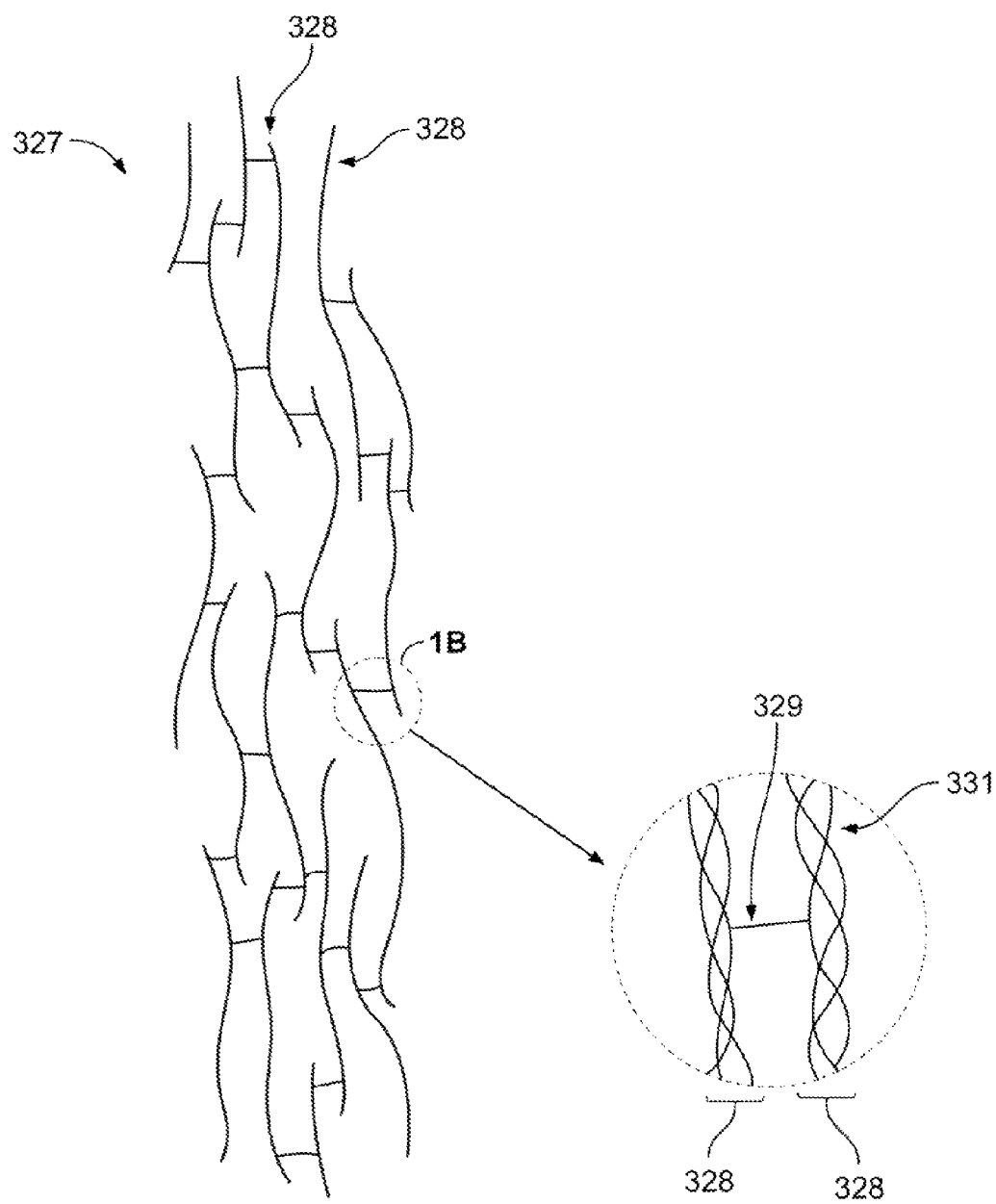
FIGS. 1A-1B show a collagenous tissue mass.
Figure 2A:
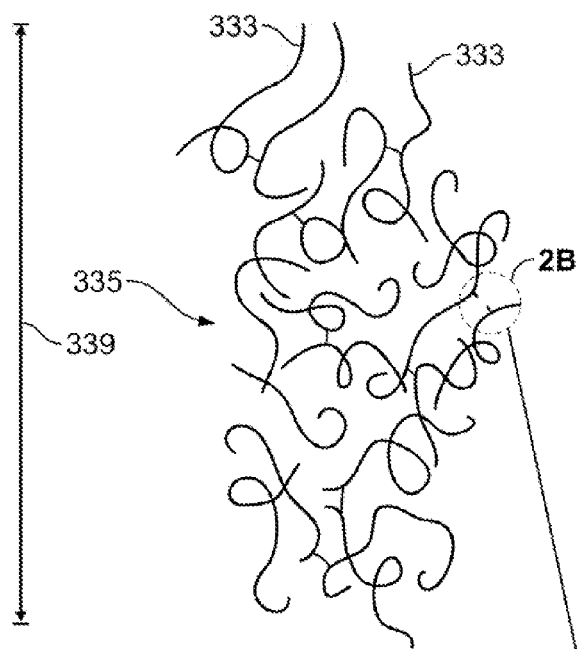
FIGS. 2A-2B show a denatured collagenous tissue mass.
Figure 2B:
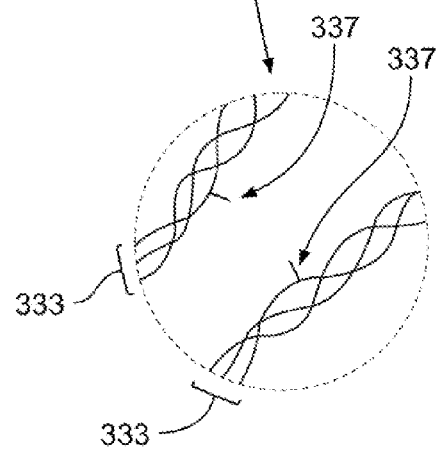
Figures 3, 4:
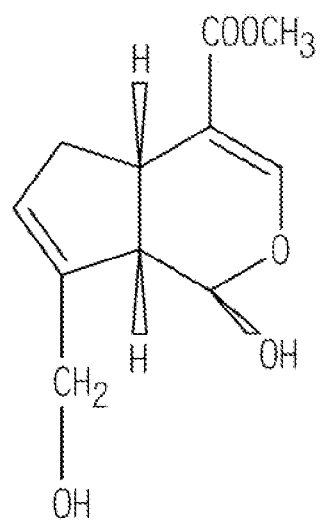
FIG. 3 shows the structure of glutaraldehyde.
FIG. 4 shows the structure of Genepin.

A variety of chemicals known as "fixatives" have, in fact, been shown to improve the mechanical strength of collagenous tissue in certain states. Many fixatives, such as leather embalmers and formaldehyde, are known to be cytotoxic, and therefore may not be idea for in-situ application. A tissue fixative known as glutaraldehyde, the structure of which is depicted in FIG. 3 (341), has been used to fix graft tissues in xenograft, allograft, or autograft scenarios before implantation. Glutaraldehyde is also cytotoxic, and further, is known to induce undesirable calcification in certain scenarios, so careful rinsing techniques are generally utilized to remove such a fixative from the tissue subsequent to pre-implantation treatment. Some porcine mitral valve xenografts, for example, are treated with glutaraldehyde fixative and rinsed before implantation. Other chemical fixatives may be more biologically inert. Genepin, an extract of plant matter used historically in Chinese medicine, has also been used as a food dye because its tends to turn proteins a blue or purple color. Some academic studies have shown that genepin, the structure of which is depicted in FIG. 4 (343), may be 5,000 to 10,000 times less cytotoxic then gluteraldehyde.

Figure 6:
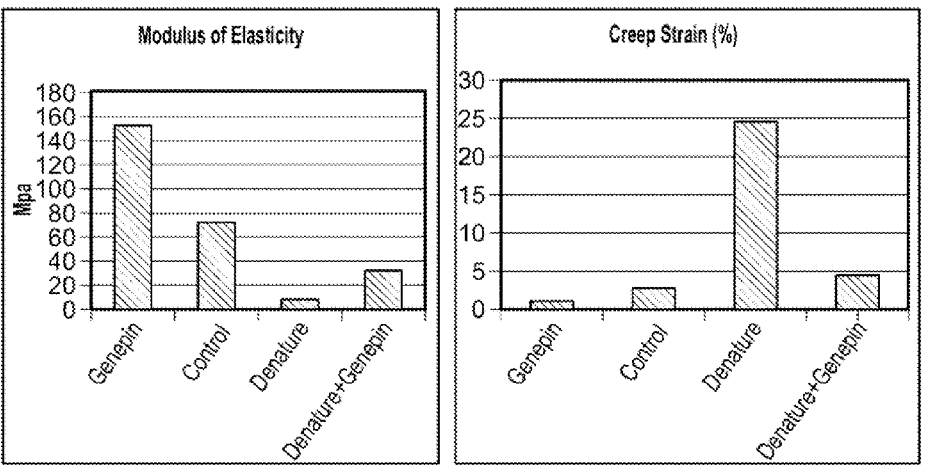
FIG. 6 shows an experiment testing denaturation accompanied by Genepin treatment.

Referring to FIGS. 5A-C, a denatured collagenous tissue mass exposed to genepin (371) is depicted. When genepin is added to collagenous tissue, the double-ring structure of genepin associates with the fibrils (333) of the collagen to produce new crosslinks (375) between fibrils, as shown in FIG. 5B, and also new crosslinks (376) between the fibers (377) comprising the fibrils, as shown in FIG. 5C. The result is a partial recovery or recreation of the mechanical properties of collagenous tissue to the state that they were prior to denaturation. In other words, denaturation accompanied by genepin treatment may result in a geometrically modified, yet stable tissue mass which is less susceptible to creep deformation than denatured collgenous tissue without genepin treatment. Referring to FIG. 6, this has been experimentally confirmed in a study at the University of Pennsylvania, as directed by the inventors of the subject invention.

Figure 7:
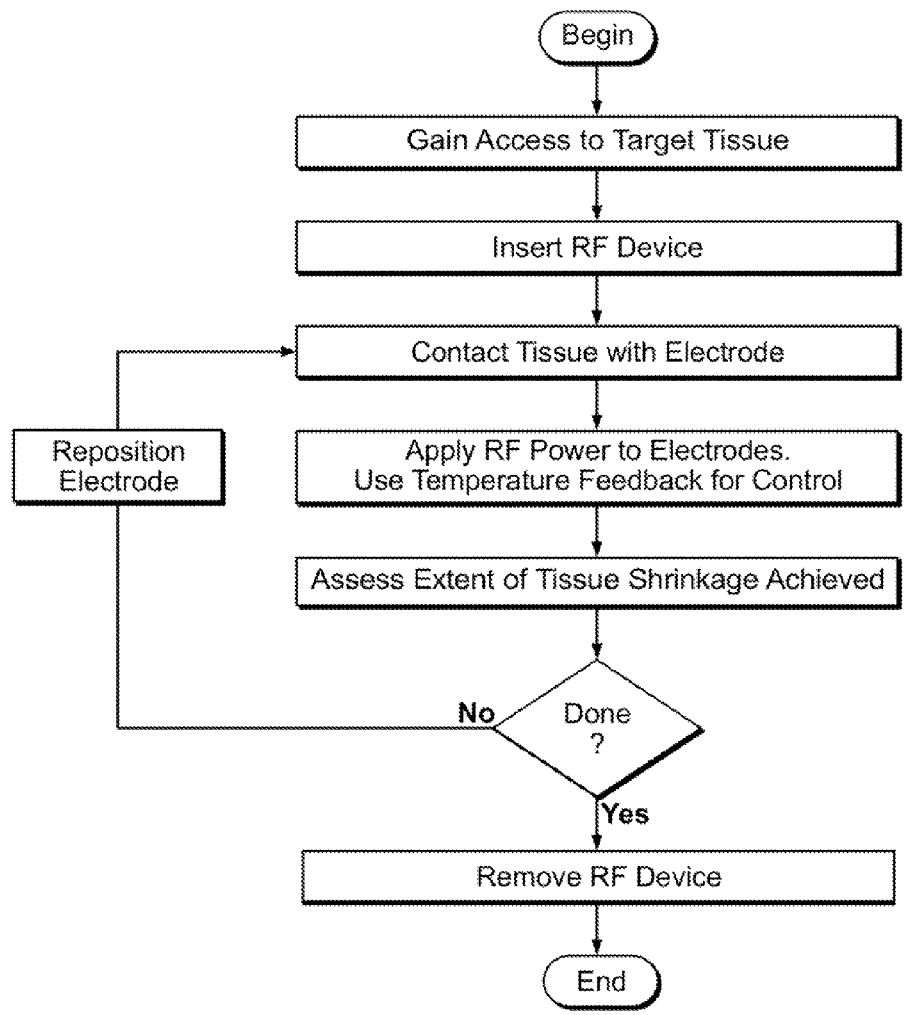
FIG. 7 shows a variation of a method for utilizing RF to denature tissue.
Figure 8:
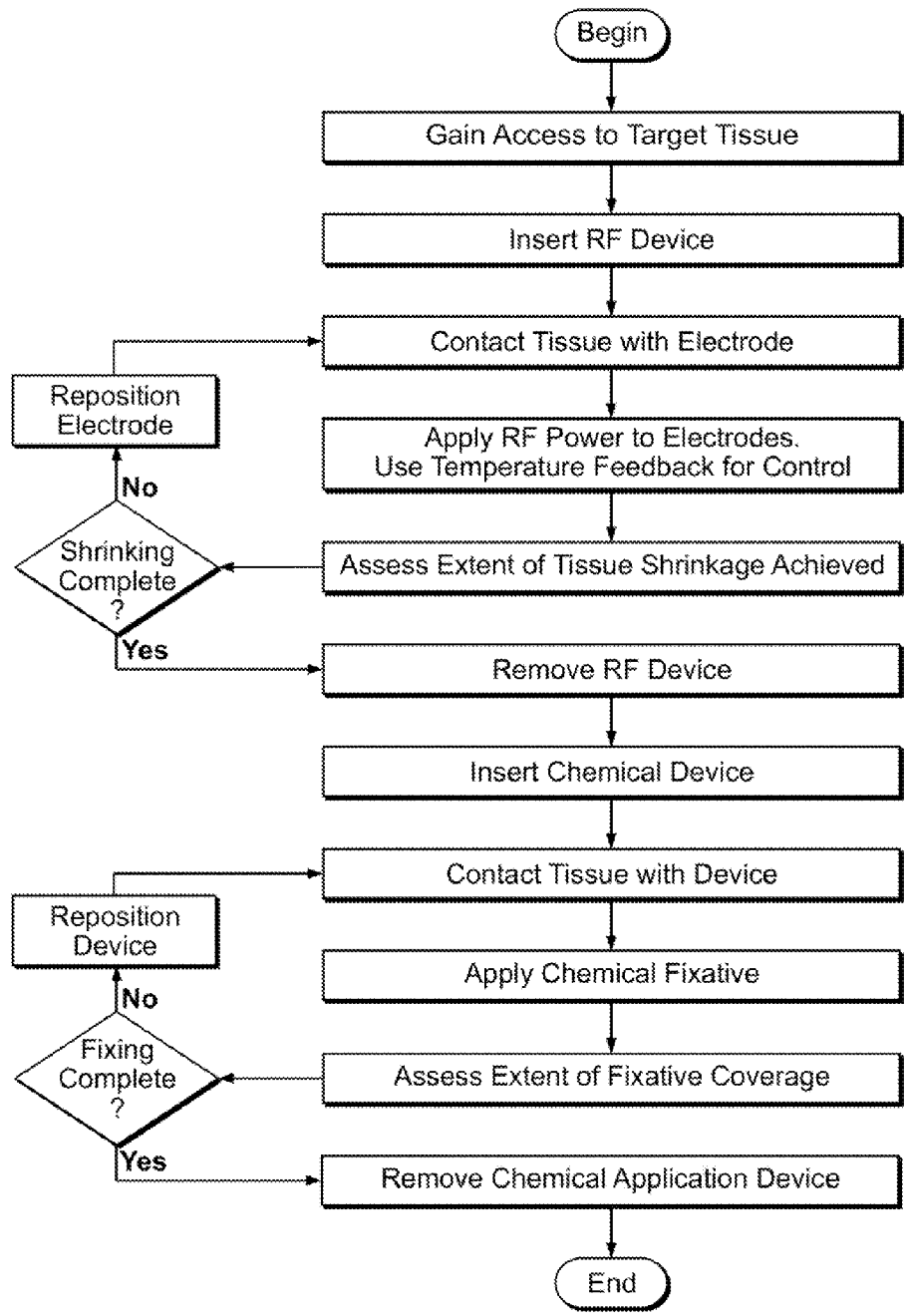
FIGS. 8-9 show variations of a method for utilizing RF to denature tissue along with Genepin fixation treatment.
Figure 9:
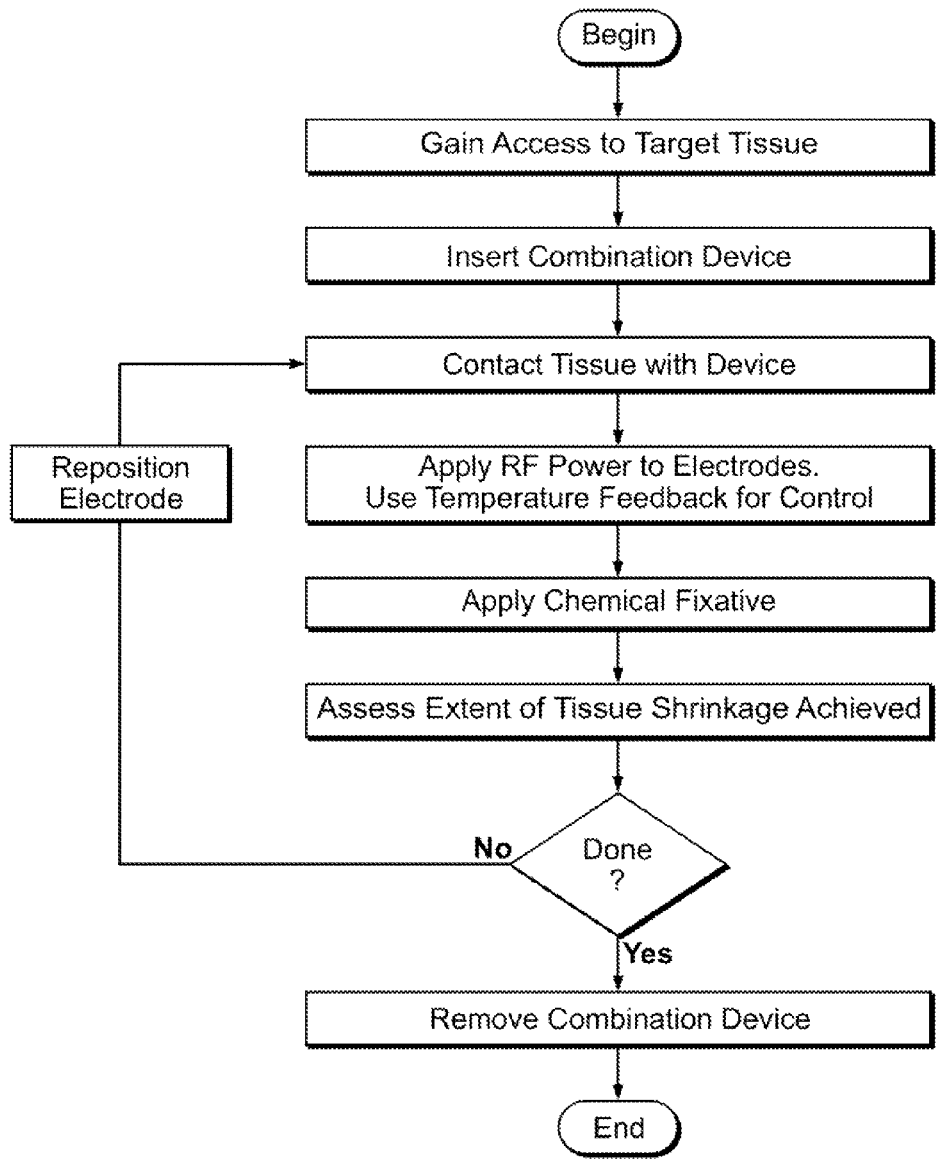
Figure 10A:
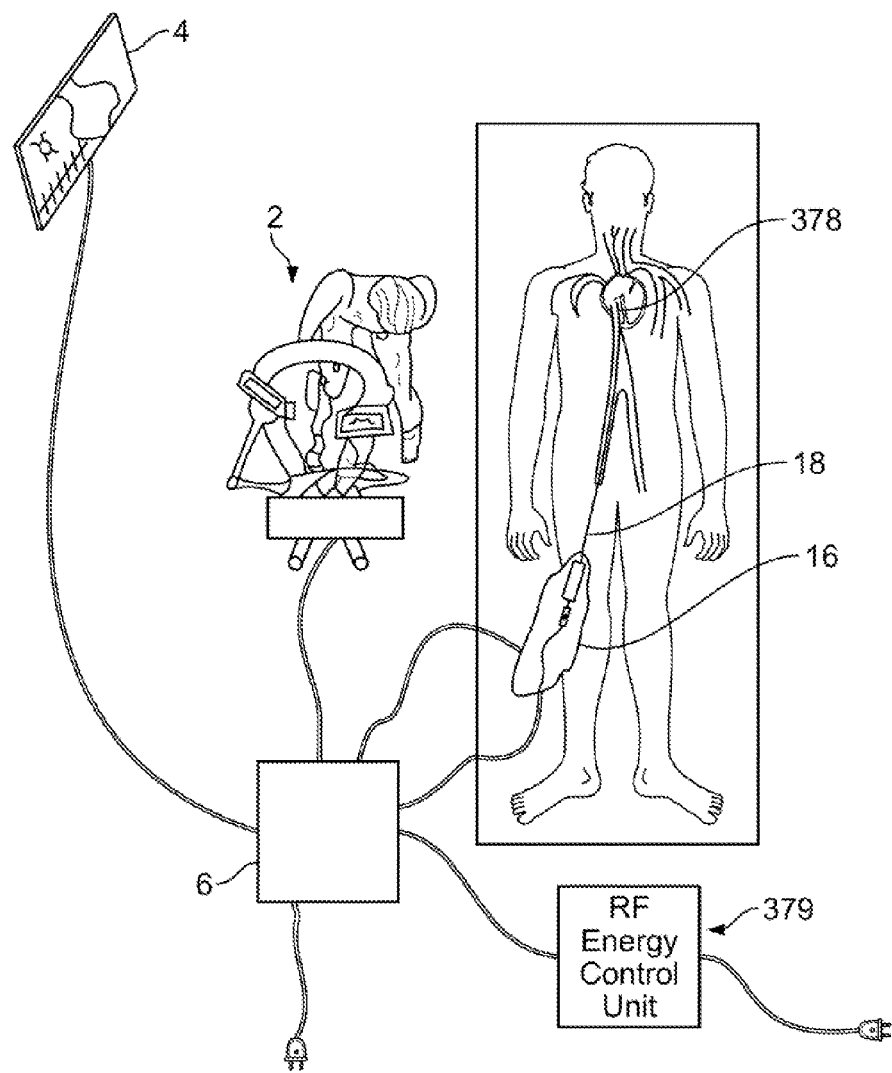
FIGS. 10A-10B shows variations of robotically controlled systems.
Figure 10B:
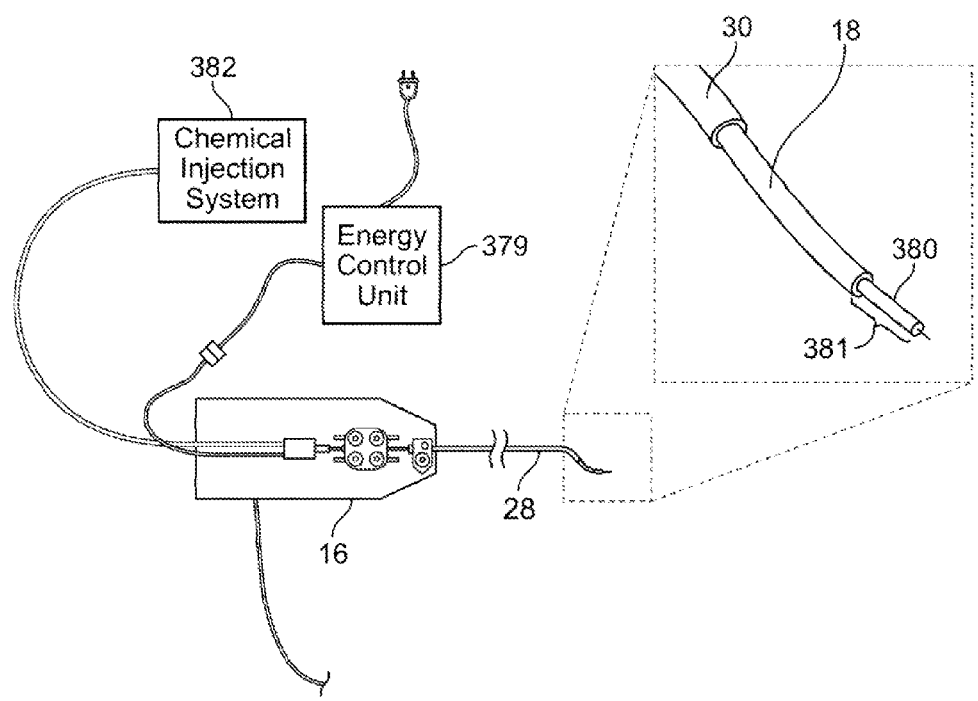

Referring to FIG. 7, one embodiment of a method for utilizing an RF device to locally denature collagenous tissue is depicted. A robotic catheter may be utilized to precisely access a targeted tissue structure, contact the targeted tissue structure with an RF electrode which may be coupled to the distal end of the robotic catheter, apply RF power to at least partially denature the subject tissue, and repeat as necessary to achieve a desired level of tissue shrinkage. Referring to FIGS. 8 and 9, embodiments utilizing genepin fixation treatment along with localized RF-induced denaturation to modify tissue geometry and recover or retain the mechanical properties of the tissue are depicted. FIG. 8 depicts an embodiment wherein a separate device is utilized to apply the denaturation treatment and genepin treatment, while FIG. 9 depicts an embodiment wherein a hybrid distal tip of the subject system may be utilized to apply both treatments without serial treatment using separate distal instrument tips for RF versus chemical fixation. Referring to FIG. 10A, a system comprising an operator control station (2), an instrument driver (16), a computer or processor (6), a display monitor (4), an elongate instrument (18) coupled to an electrode (378), and an RF energy control unit (379) is depicted. Such a system may be utilized for the embodiment depicted, for example, in FIG. 7. In alternative embodiments, other modalities may be utilized, such as ultrasound or microwave radiation, or heated fluids such as hot saline, to produce localized heating at the distal end of the elongate instrument (18) for denaturation of collagenated tissue. Referring to FIG. 10B, a similar system is depicted comprising an instrument driver (16) interfaced to an instrument set (28) comprising coaxially-interfaced sheath (30) and guide (18) instruments. The guide instrument (18) is coaxially interfaced, through its inner lumen, with an elongate probe (380) which may comprise a heating and/or injecting tool at its distal tip (381). In an embodiment comprising an injecting tip, a chemical injection system (382) may be proximally coupled to the instrument set (28) and configured to controllably deliver fluid, such as a genepin formulation, through the injecting tip distally.

Figure 11F:
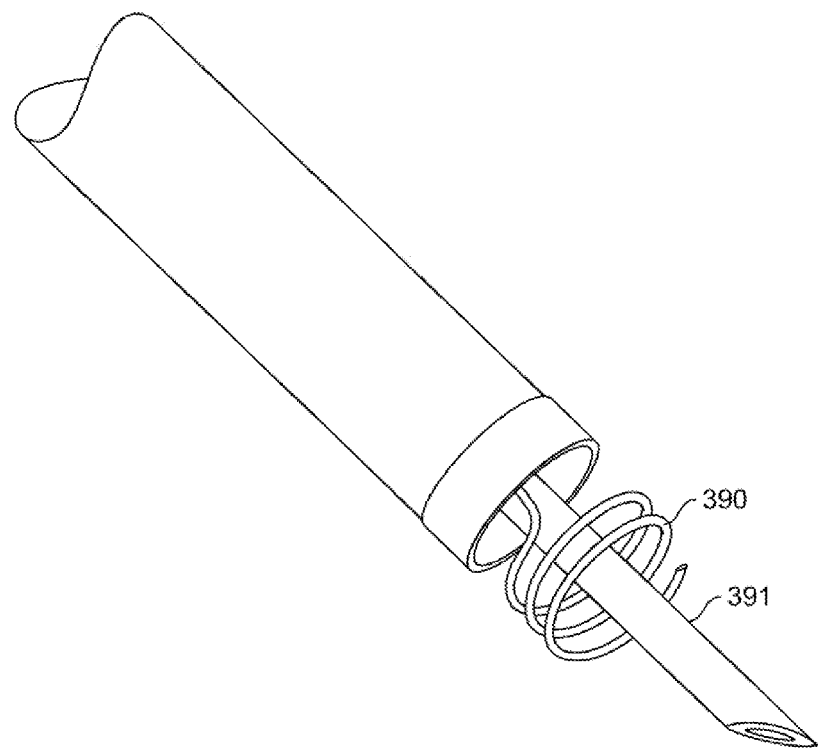
Figure 11G:
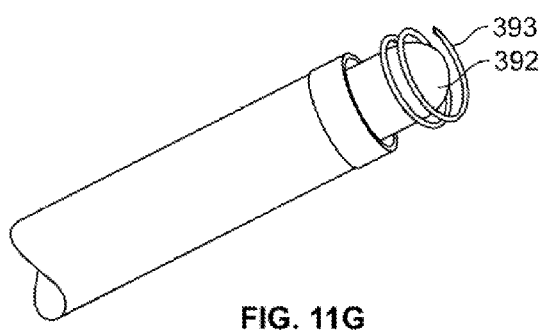
Figure 11H:
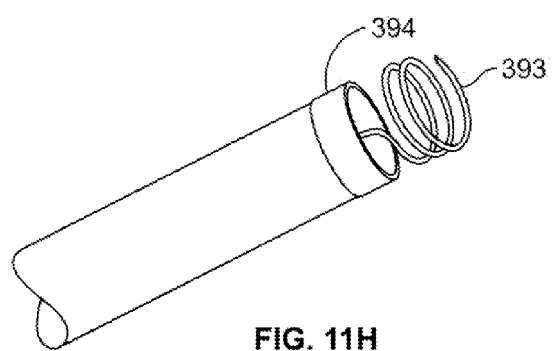

Referring to FIG. 11A-H, various hybrid distal tip structures for an elongate instrument configured to both inject a chemical solution, such as a genepin solution or solution of another fixative, and also apply RF energy to induce localized denaturation are depicted. FIG. 11A depicts a needle-less injection port (384) positioned through the center of a monopolar RF electrode (383). FIG. 11B depicts a series of needle injection ports (385) located upon an RF electrode (383) for a voljimic injection into a broader volume that would be practicable with a single needle. FIG. 11C depicts an extensible/retractable needle (386) injection port through the center of an RF electrode (383). FIG. 11D depicts bipolar electrode configuration wherein each of two distal elements (387) comprises both an electrode and an injection tip. FIG. 11E depicts a single injection needle through the center of an RF electrode (383), the needle (388) comprising multiple fluid pathways (389) along its length to facilitate a distributed injection through a depth of targeted tissue. The needle (388) may be extensible/retractable, as with each of the distal tip needle structures depicted herein. FIG. 11F depicts an embodiment wherein an injection needle (391) is oriented through the center of a helical structure (390), and wherein any of the distal elements may be an RF electrode—in other words, the injection needle (391) or helical structure (390) may be a monopolar electrode, or each may be an electrode in a bipolar configuration. FIG. 11G depicts an embodiment wherein a bullet-shaped electrode (392) is positioned through at least a portion of a helical injection needle (393). FIG. 11H depicts an embodiment similar to that of FIG. 11G with the exception that a distal ring (394) comprises the electrode as opposed to the bullet-shaped electrode of FIG. 11G. The helical injection needles of the embodiments depicted in FIGS. 11G and 11H may have side ports (not shown) as depicted in the embodiment of FIG. 11E, and may comprise an electrode form a bipolar electrode configuration in association with the bullet-shaped electrode (392) or ring electrode (394).

Figure 12A:
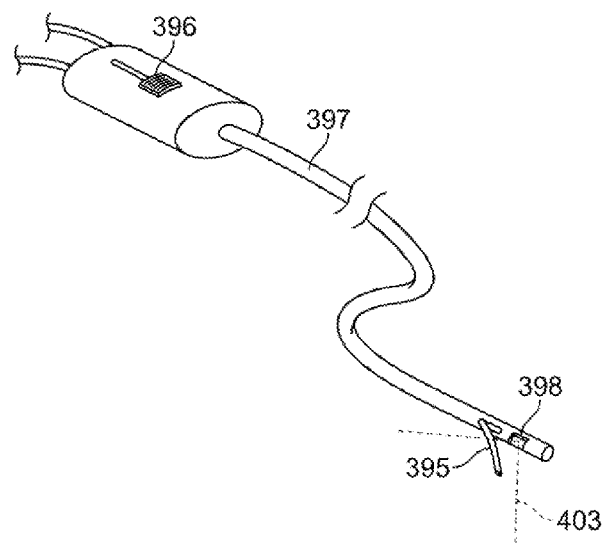
FIGS. 12A-C show variations of a system having a retractable injection needle extendable from the side of an elongate probe.
Figure 12B:
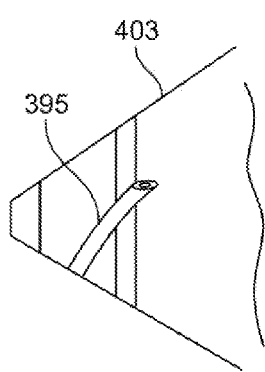
Figure 12C:
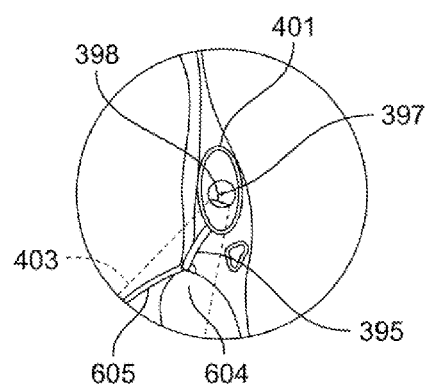

Referring to FIGS. 12A-C, a retractable injection needle (395) may be retractably extended from the side of an elongate probe (397) to provide access to tissue structures located to the periphery of a given probe orientation, such as the mitral annulus as oriented from the coronary sinus, as depicted in FIG. 12C. The injection needle (395) may be advanced and/or retracted utilizing a simple proximal mechanical lever (396), as depicted in FIG. 12A, or may be associated with an electromechanical configuration for precisely actuating advancement and/or retraction. To facilitate accurate positioning of a side-extending injector, or injector which also comprises an electrode in another embodiment, an imaging device (398), such as an ultrasound array, CCD device, or more conventional optical camera, in one embodiment comprising a mirror for side-oriented field of view (403), may be coupled to the probe (397) to provide a field of view (403) configured to capture images of at least a portion of the needle or needle/electrode as it is advanced out of the probe (397), as depicted in FIG. 12B. Referring to FIG. 12C, a partial cross sectional view of a system such as that depicted in FIGS. 12A and 12B is depicted with the probe (397) threaded down a coronary sinus (401) of a human heart, and an injection needle (395), in this embodiment also comprising an electrode, directed out of the coronary sinus (401) lumen and into the collagenous mitral valve annulus (604). The field of view (403) of the imaging device (398), in the depicted embodiment comprising an ultrasound transducer, is oriented to capture images of at least a portion of the needle (395), and preferably portions of surrounding identifiable tissues, such as the mitral annulus (604) or mitral valve leaflet (605).

Referring to FIGS. 13A-18D, several embodiments of systems and methods for minimally-invasive soft tissue shrinking interventions are depicted.

Figure 13A:
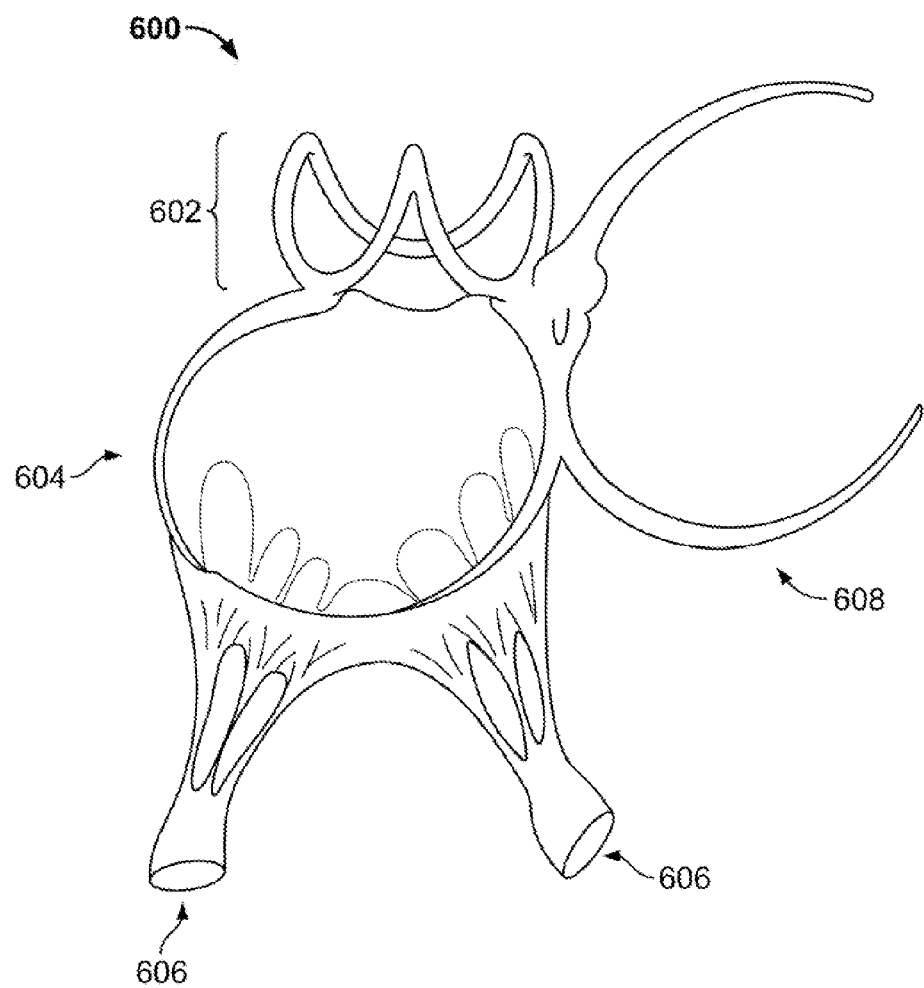
FIGS. 13A-C shows endoskeletons of the heart.
Figure 13B:
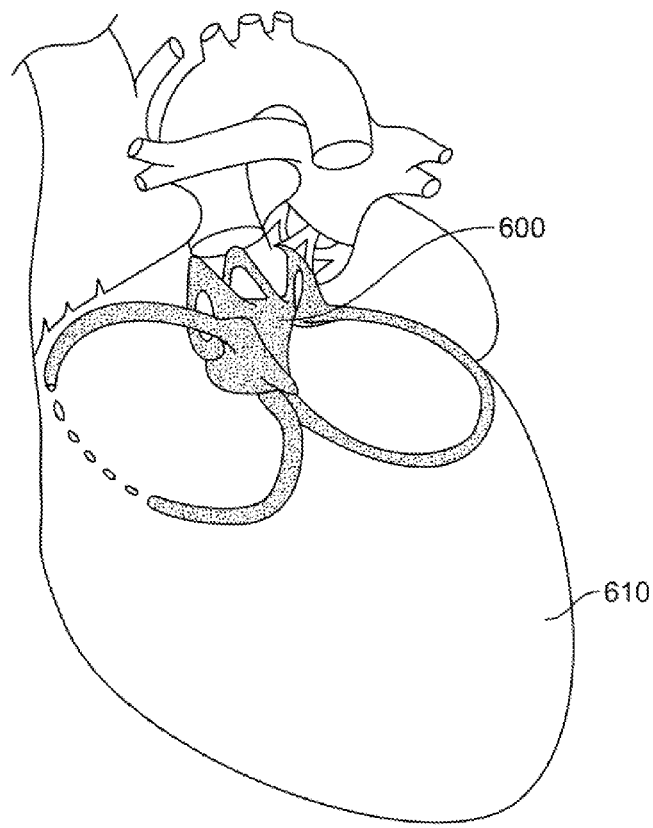

The inventive system may be utilized to address problems associated with mitral valve annulus deformation, such as mitral regurgitation. Referring to FIG. 13A, a structure which may be referred to as the "endoskeleton" of the heart is depicted (600), comprising three soft tissue backbones for the cusps of the aortic valve (602), the soft tissue backbone of the mitral valve annulus (604), pappilary muscle and chordae tendonae complexes (606), and the soft tissue backbone of a partial tricuspid valve annulus (608). Referring to FIG. 13B, an endoskeleton (600) is depicted in situ, surrounded by the anatomy of a normal human heart (610). The endoskeleton (600) may be described as a rather tough, gristle-like structure somewhat akin to the cartilage of the human ear. It is believed to hold the valves in position relative to each other and act as the primary load-bearing structure of the heart (610). Not by accident, it is the target destination of sutures placed by a surgeon utilizing conventional surgical techniques to address problems such as mitral valve deformation and associated functional mitral regurgitation, whereby there may be nothing intrinsically wrong with the mitral valve, but secondary to congestive heart failure, for example, the heart enlarges, pulling out the posterior leaflet of the mitral valve, thereby creating a lack of coaptation of the leaflets. Such coaptation problems generally are the result of deformation of the posterior aspect of the mitral annulus, as opposed to the anterior portion.

Figure 13C:
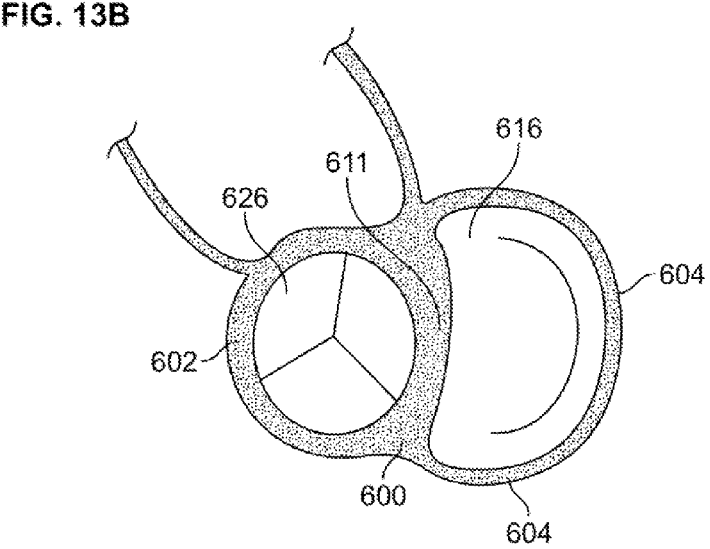

Referring to FIG. 13C, a subportion of an endoskeleton (600) is depicted at an angle to illustrate the curved posterior mitral annulus structure (604) versus the anterior aspect (611) of the mitral annulus structure, which comprises one of the central constructs of the endoskeleton (600). The aortic valve (602) annulus structure (626) is located opposite this central construct from the mitral valve (603).

Figure 13D:
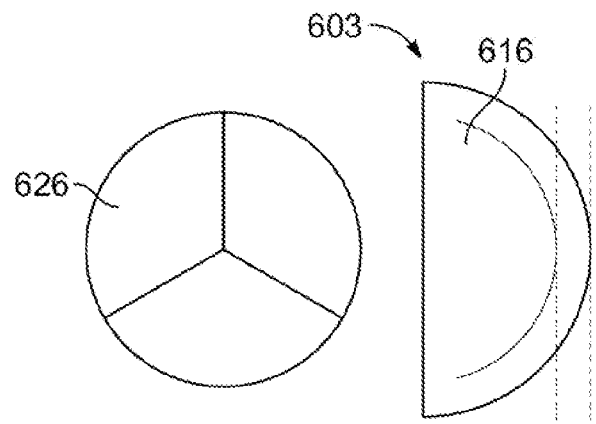
FIGS. 13D-E show various states of coaptation of a valve.
Figure 13E:
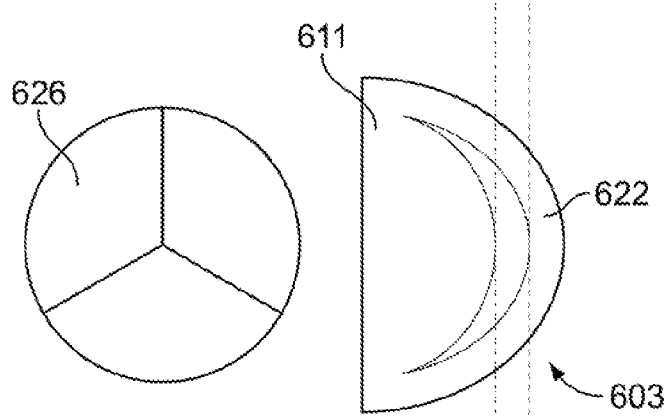
Figure 13F:
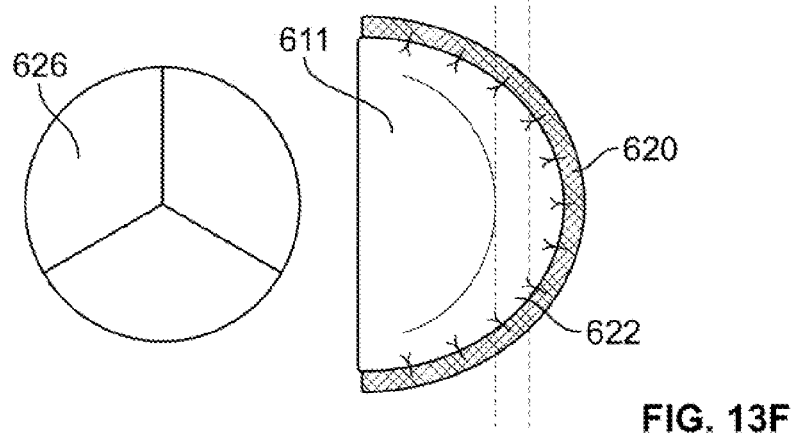
FIGS. 13F-G shows various prostheses for valves.
Figure 13G:
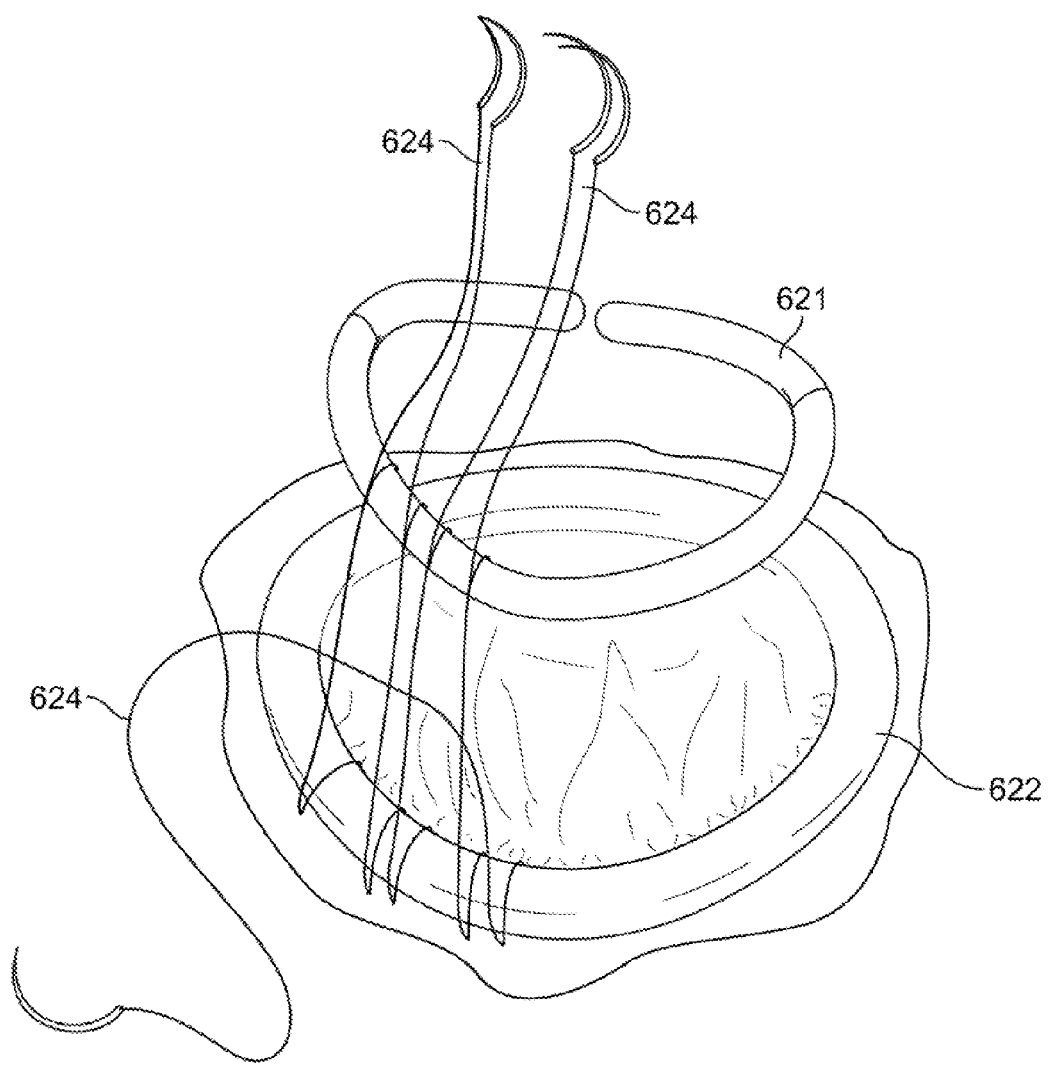

Referring to FIG. 13D, a mitral valve (603) is depicted with good coaptation when closed. A well-coated tricuspid valve (626) is also depicted. FIG. 13E depicts a similarly-sized mitral valve (603) with a significant leaflet coaptation problem when closed, primarily due to deformation of the posterior aspect (622) of the mitral annulus, as opposed to significant deformation of the anterior aspect (611) of the mitral annulus. Such posterior mitral annulus deformation conventionally may be treated with installation of an annulus reshaping prosthesis, such as that depicted in FIG. 13F. Conventional prostheses for this purpose take many forms, including configurations such as that depicted in FIG. 13F, wherein the prosthesis only substantially supports the posterior aspect (622) of the mitral annulus, and configurations such as that depicted in FIG. 13G, wherein the prosthesis (621) supports substantially all of the mitral annulus. Referring to FIG. 13G, the depicted conventional prosthesis (621), such as those known as a "Carpintier ring", may be installed with a series of sutures (624) configured to gather and pull the posterior annulus (622) tissue anteriorly when the prosthesis (621) has been fastened into place. One of the challenges associated with such an installation is the invasiveness of the procedure. To address this challenge, the inventive instrument may be utilized to intravascularly approach the mitral annulus and treat the tissue to modify its geometry with minimal invasiveness relative to conventional open or port-based procedures.

Figure 13H:
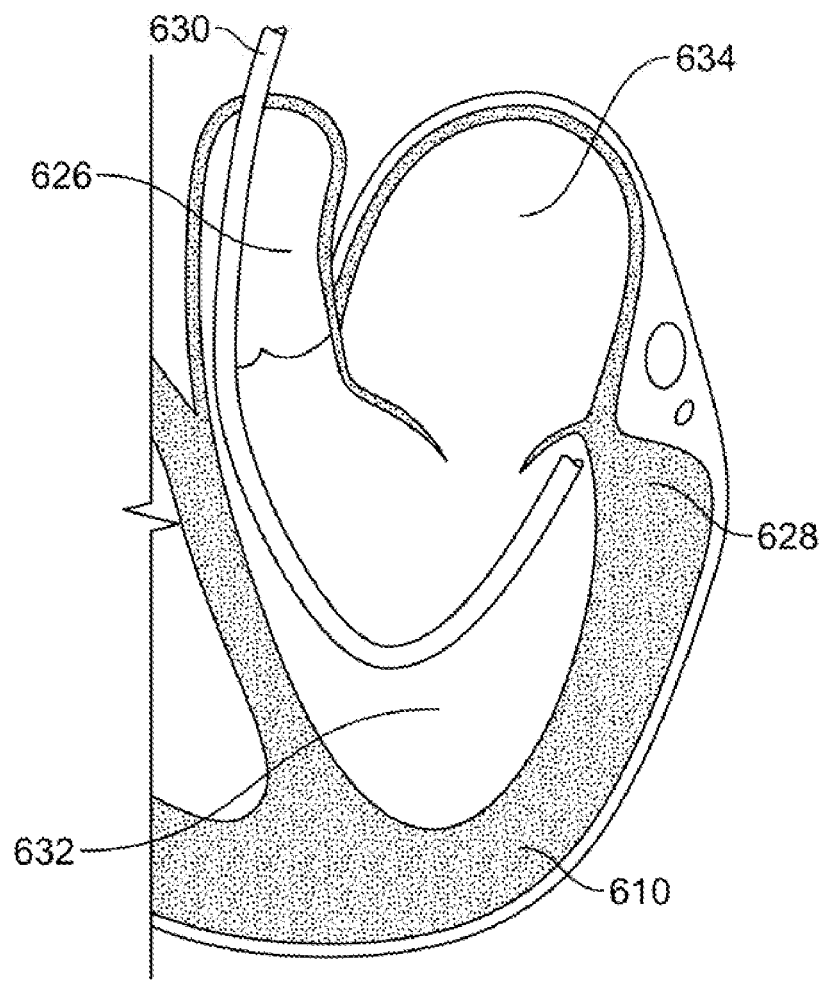
FIGS. 13H-L show various access approaches to a valve annulus or valve.

Referring to FIG. 13H, an arterial access route is depicted whereby an elongate steerable instrument (630) such as that described above may be utilized to pass across the aortic valve (602), turn, and extend up toward the underside of the mitral annulus (628), thereby providing access to the underside, or inferior aspect, of the mitral valve annulus.

Figure 13I:
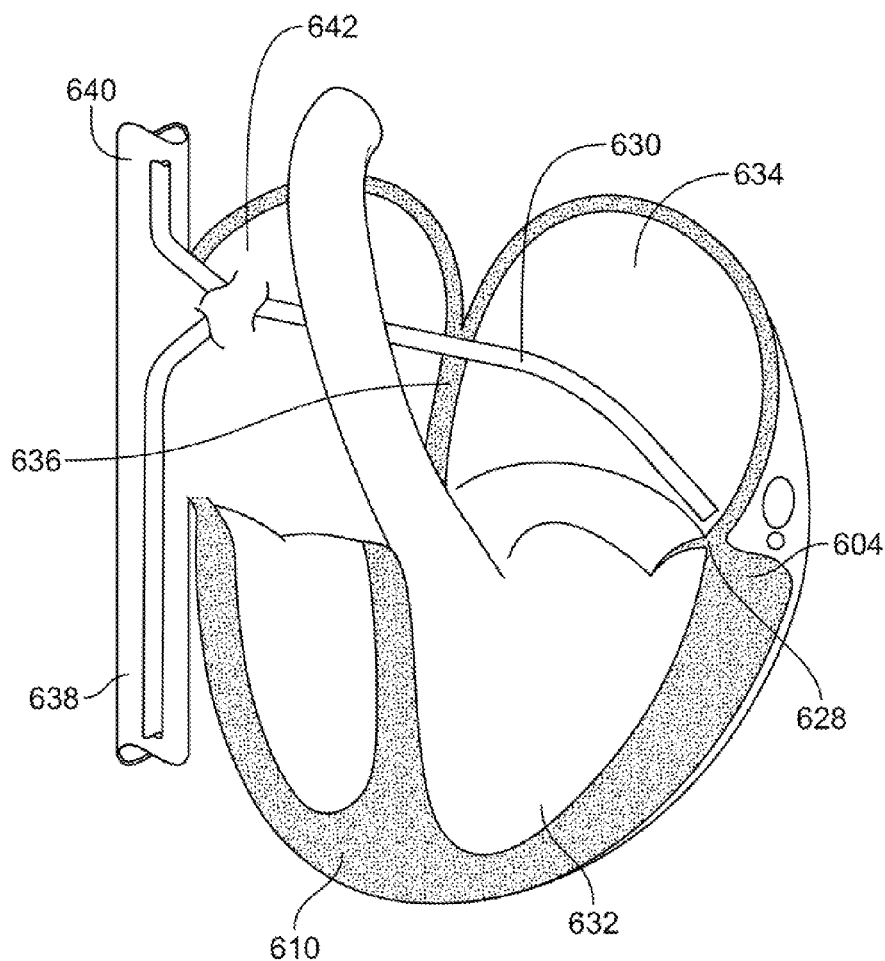
Figure 13J:
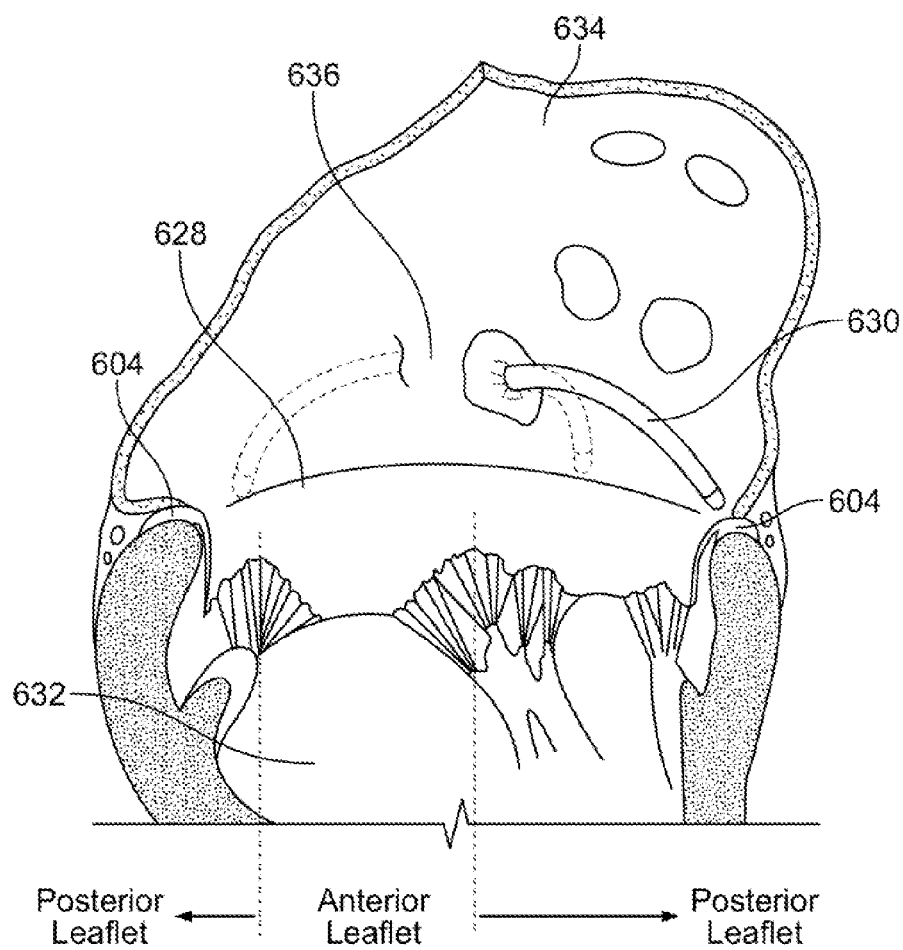

Referring to FIGS. 13I-J, a trans-septal approach to the superior aspect of the mitral annulus is depicted whereby an elongate steerable instrument (630) such as that described above may be utilized to pass across the right atrium (642) as it exits either the inferior (638) or superior (640) vena cava, cross the septum (636), and cross the left atrium (634) as it extends over to the top aspect (628) of the mitral valve annulus (604). Referring to FIG. 13J, a partial sectional view of structures similar to those depicted in FIG. 13I are depicted to illustrate that a steerable elongate instrument (630) with sufficient control and steerability may be used to contact various superior aspects (628) of the mitral valve annulus (604), from this trans-septal approach.

Figure 13K:
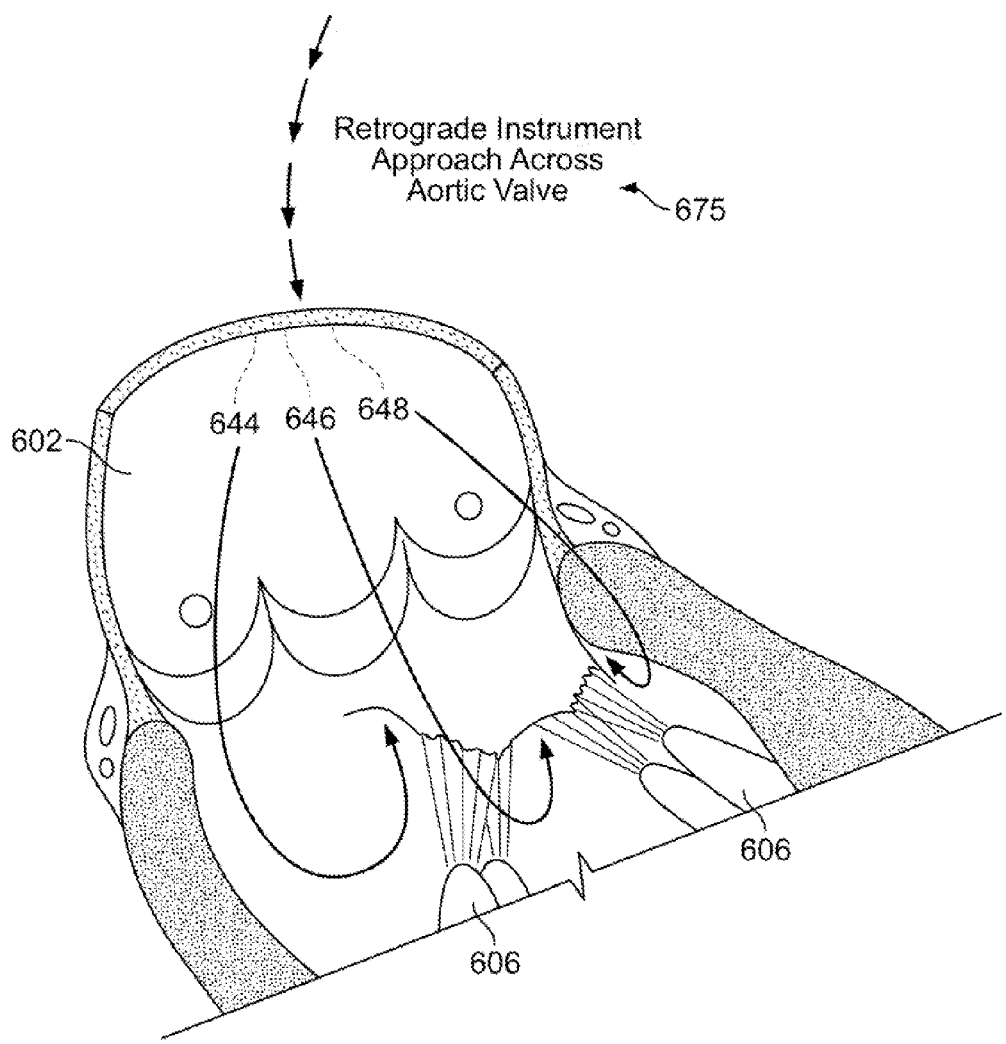
Figure 13L:
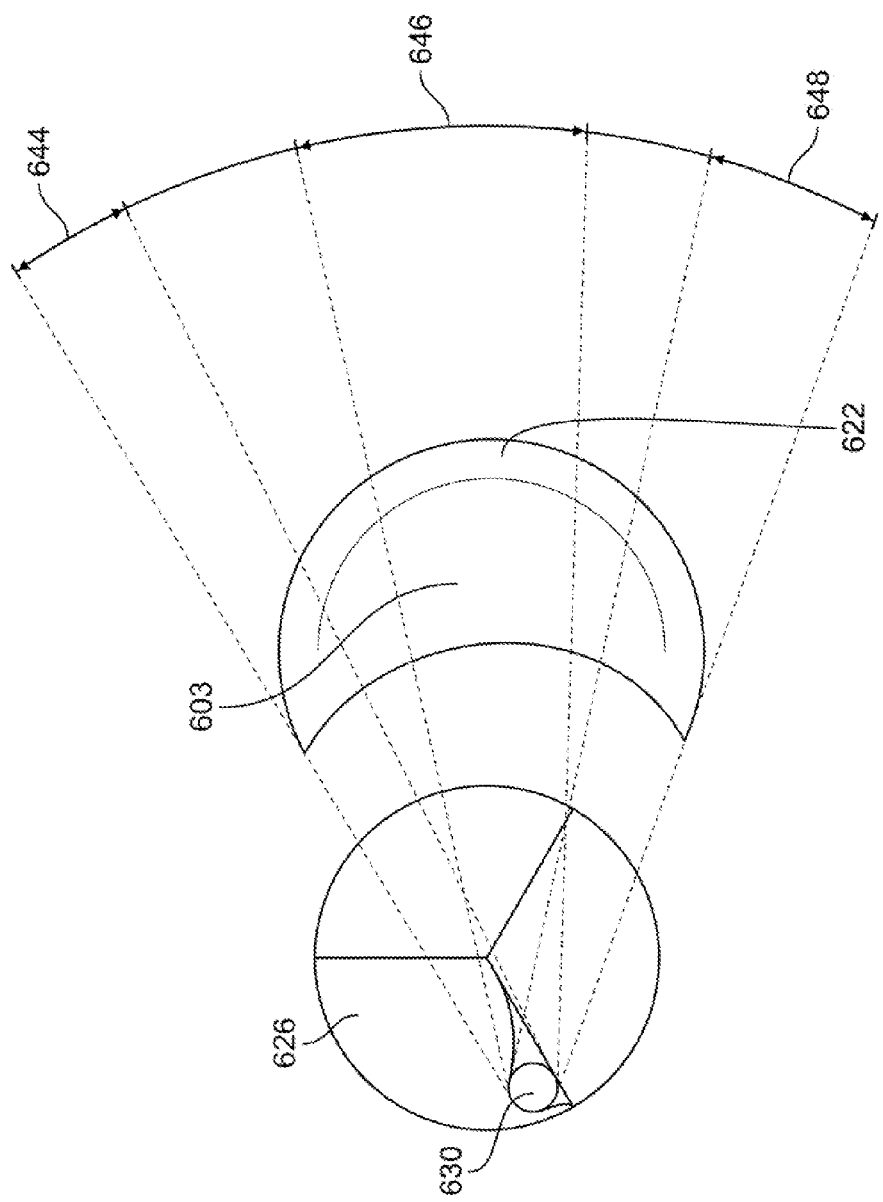

FIGS. 13K and 13L depict further detail regarding an underside approach to the mitral valve annulus such as that discussed in reference to FIG. 13H. Referring to FIG. 13K, utilizing an arterial retrograde approach (675) across the aortic valve (602), the aortic valve (602) shown split open in FIG. 13K, a steerable elongate instrument such as those described herein may follow one of three pathways (644, 646, 648) to access various aspects of the mitral annulus: to the left (644) of the papillary/chordae (606), to the right (648) of the papillary/chordae (606), or in between (646) the papillary/chordae (606). Referring to FIG. 13L, a schematic view illustrates that by utilizing the approaches depicted in FIG. 13K, a flexible elongate instrument (630) passed through the aortic valve (602) may access nearly all of the mitral valve annulus utilizing one of the three pathways (644, 646, 648) depicted in FIG. 13K, which are selected to avoid transverse motion and entanglement in the papillary/chordae (606) and other structures of the beating heart mitral valve (603) complex.

Thus superior/trans-septal and inferior/aortic approaches to the collagenous tissue structures of the mitral annulus, including but limited to the posterior aspect of the mitral annulus, are described in reference to FIGS. 13I-J, and 13H, J, and L. From each illustrated approach, a steerable elongate instrument may be utilized to access, denature, and/or chemically fix tissues of the mitral annulus utilizing distal tip hardware such as the embodiments described in reference to FIGS. 11A-H, and techniques such as those described in reference to FIGS. 7-9.

Figure 14A:
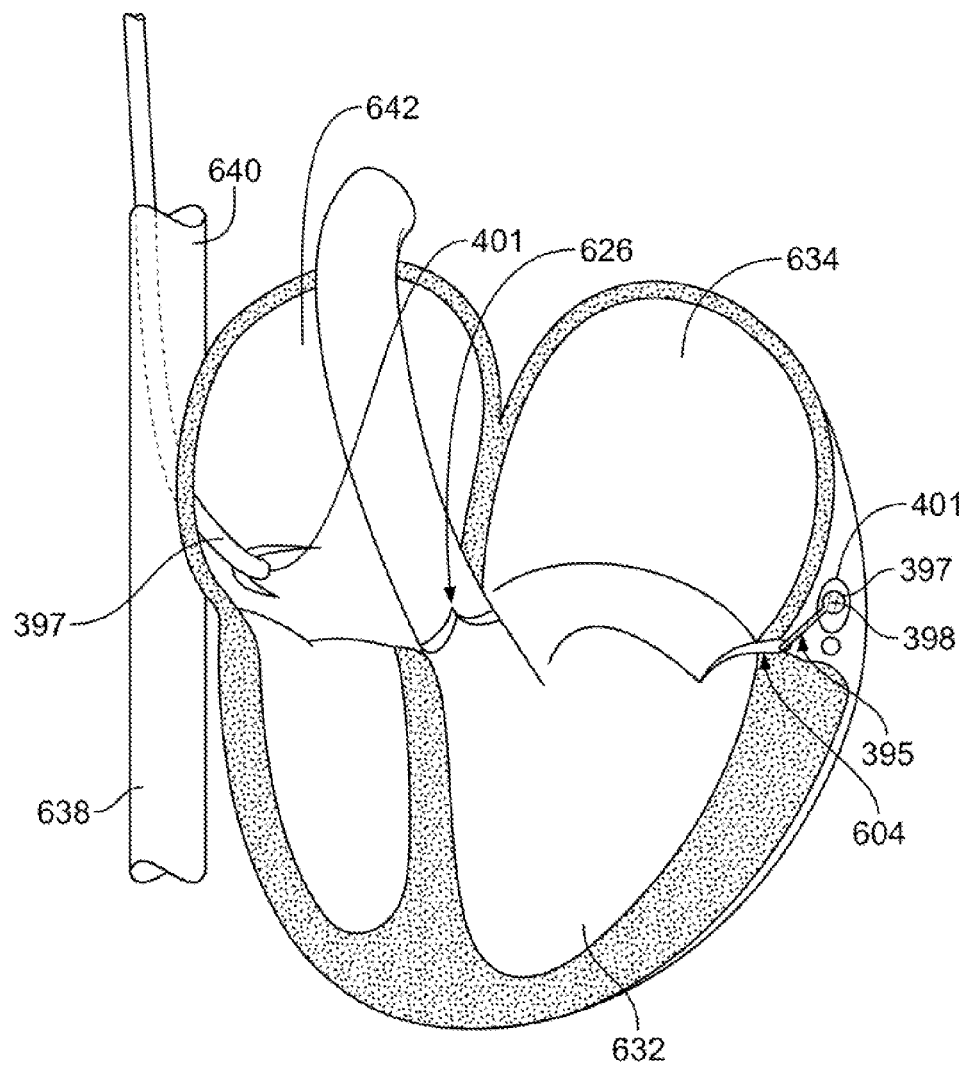
FIGS. 14A-C show access approaches to a valve annulus or valve via a coronary sinus.
Figure 14B:
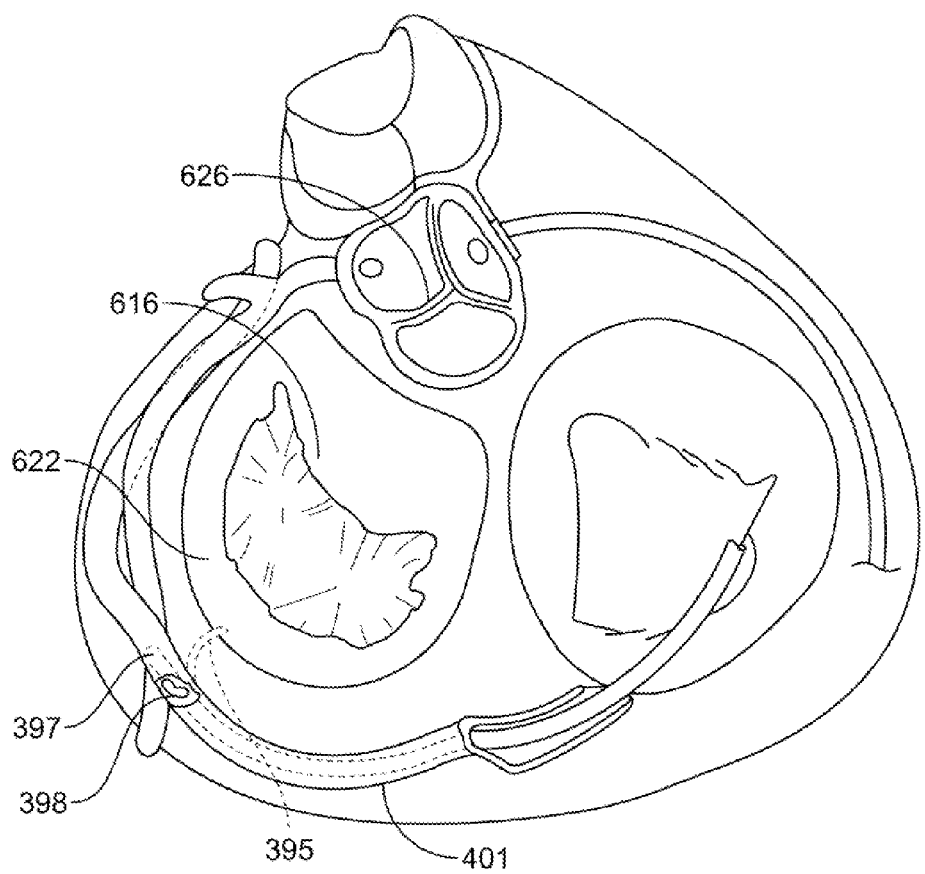
Figure 14C:
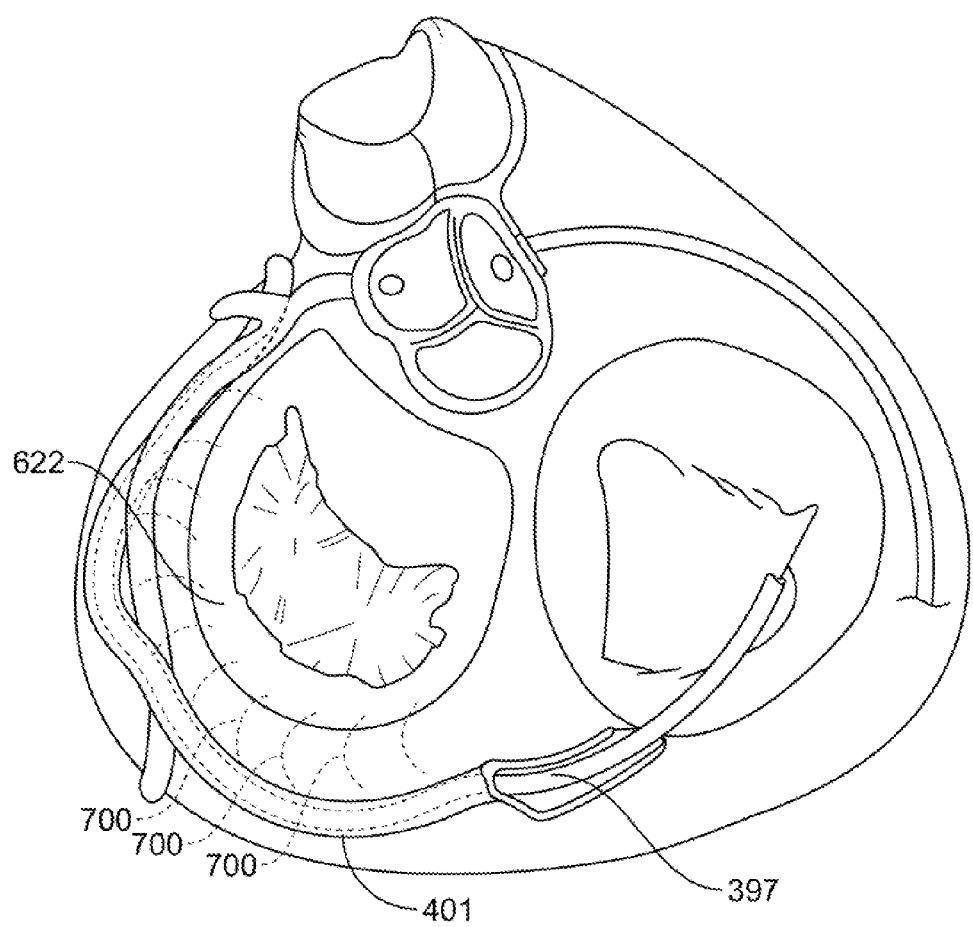

In another embodiment, a system comprising a probe configuration such as that depicted in FIGS. 12A-C may be utilized to cannulate the coronary sinus and access the collagenous tissue of the mitral valve by crossing out of the coronary sinus with a protruding needle device. Referring to FIG. 12A, a flexible probe instrument (397) may be directed into the coronary sinus (401) from the right atrium (642) and advanced through the coronary sinus (401) to place a advanceable/retractable injection and/or electrode needle (395) out the side of the probe (397), across the field of view of an imaging device (398), and into at least a portion of the collagenous tissue comprising the posterior mitral valve annulus (622), as depicted in FIG. 14B, where such collagenous tissue may be locally denatured and/or chemically fixed to provide retained tightening of the posterior annulus tissue, and preferably better coaptation of the mitral valve. As shown in FIG. 14C, the probe (397) may be advanced through the coronary sinus (401) to provide the needle (395) with a broad pattern (700) of access to portions of the posterior mitral annulus (622) to provide a series of localized shrinkings which together provide circumferential shrinking of the posterior mitral annulus (622), and thereby better mitral valve leaflet coaptation. Mitral regurgitation (not shown) may be observed with ultrasound as the posterior mitral annulus local shrinking is conducted, as depicted in FIG. 14C, for example, to provide the operator with realtime feedback as to the effectiveness of localized "tuning" and appropriate next steps during the operation.

Figure 15A:
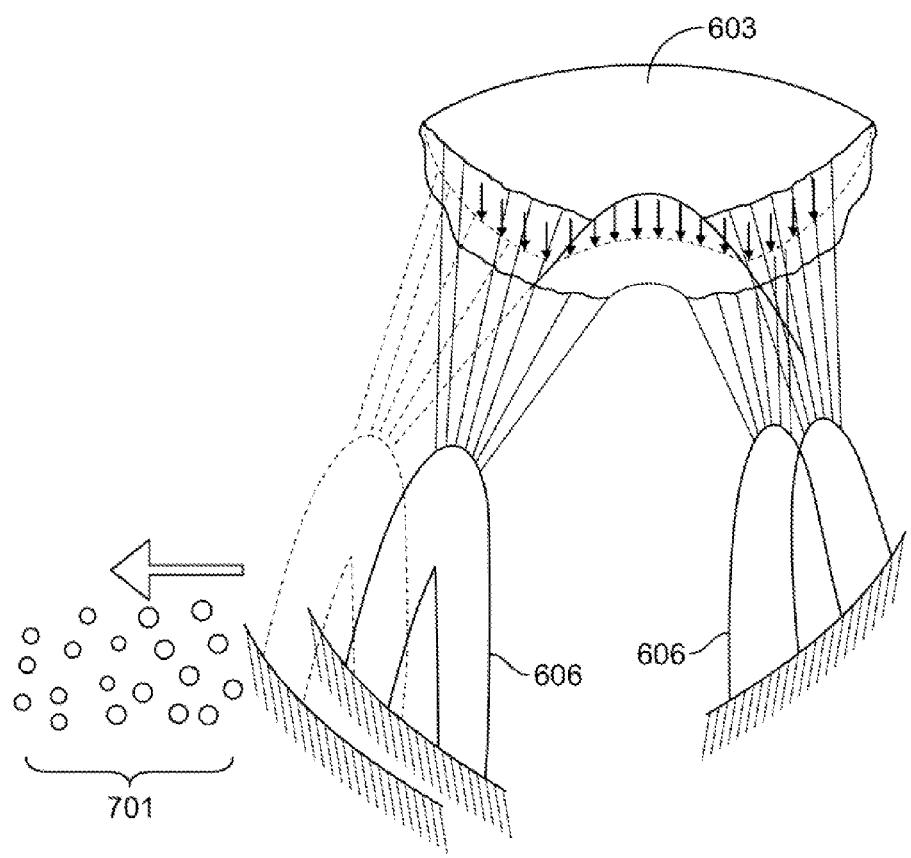
FIGS. 15A-B show localized denaturation for adjusting the position of chordae complexes.
Figure 15B:
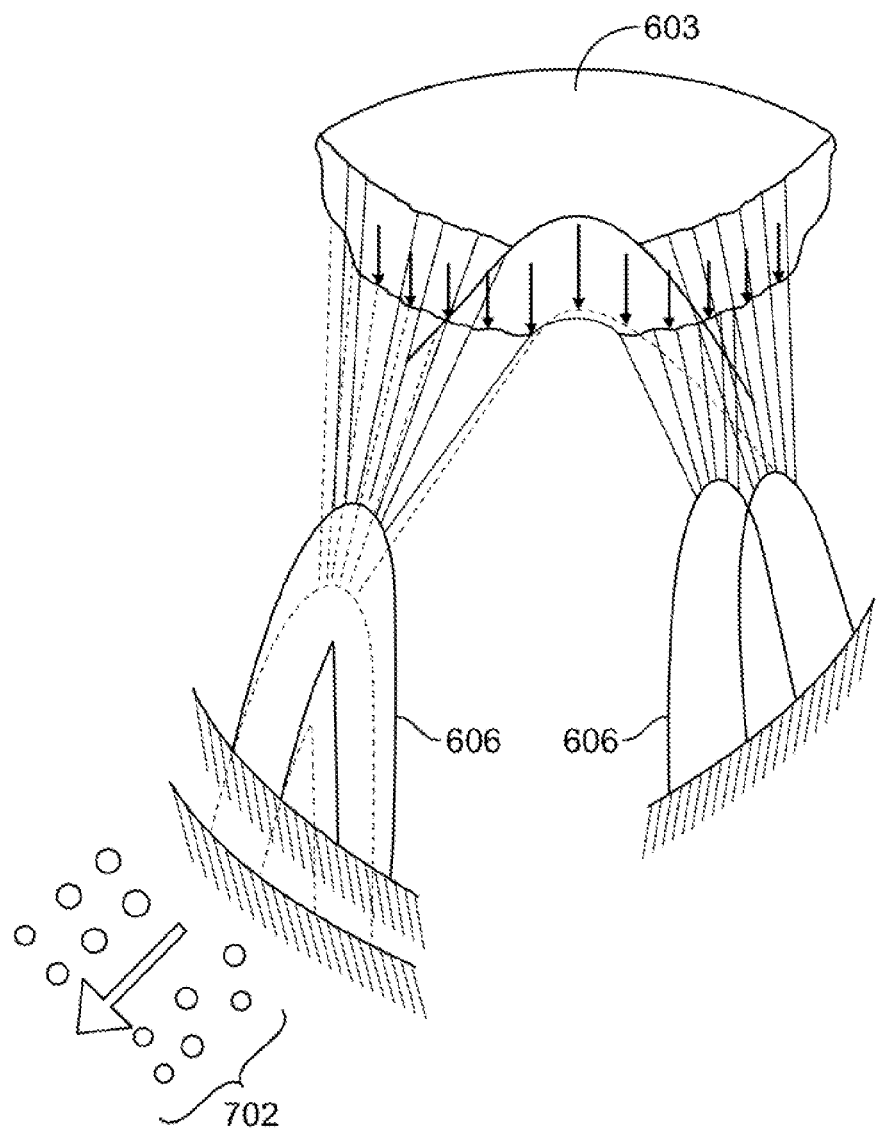

Referring to FIG. 15A, a field of tissue lesions (701) treated by localized denaturation, chemical fixation, or both, may be utilized to slightly adjust the position of one of the papillary/chordae complexes (606) sideways relative to the mitral valve (603) to adjust valve coaptation. Similarly, as depicted in FIG. 15B, a differently-positioned field of tissue lesions (702) may be utilized to adjust the position of one of the papillary/chordae complexes (606) downward, or sideways and downward, relative to the mitral valve (603) position to adjust valve coaptation.

Figure 16A:
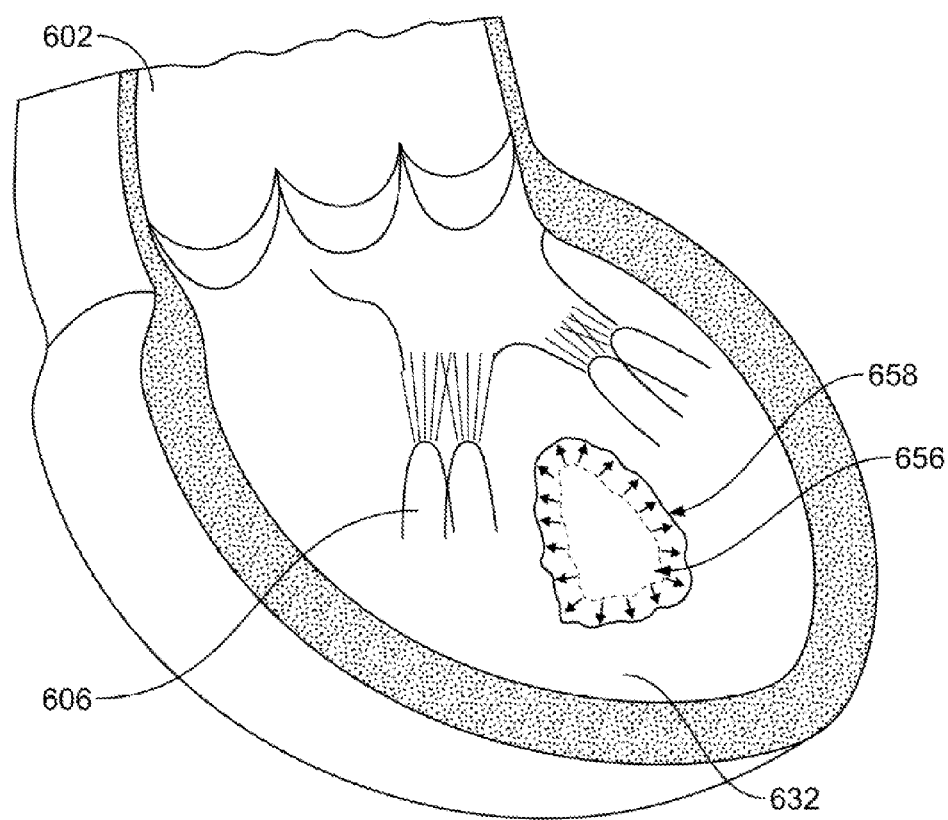
FIGS. 16A-F show various systems for addressing deformation due to infarction.
Figure 16B:
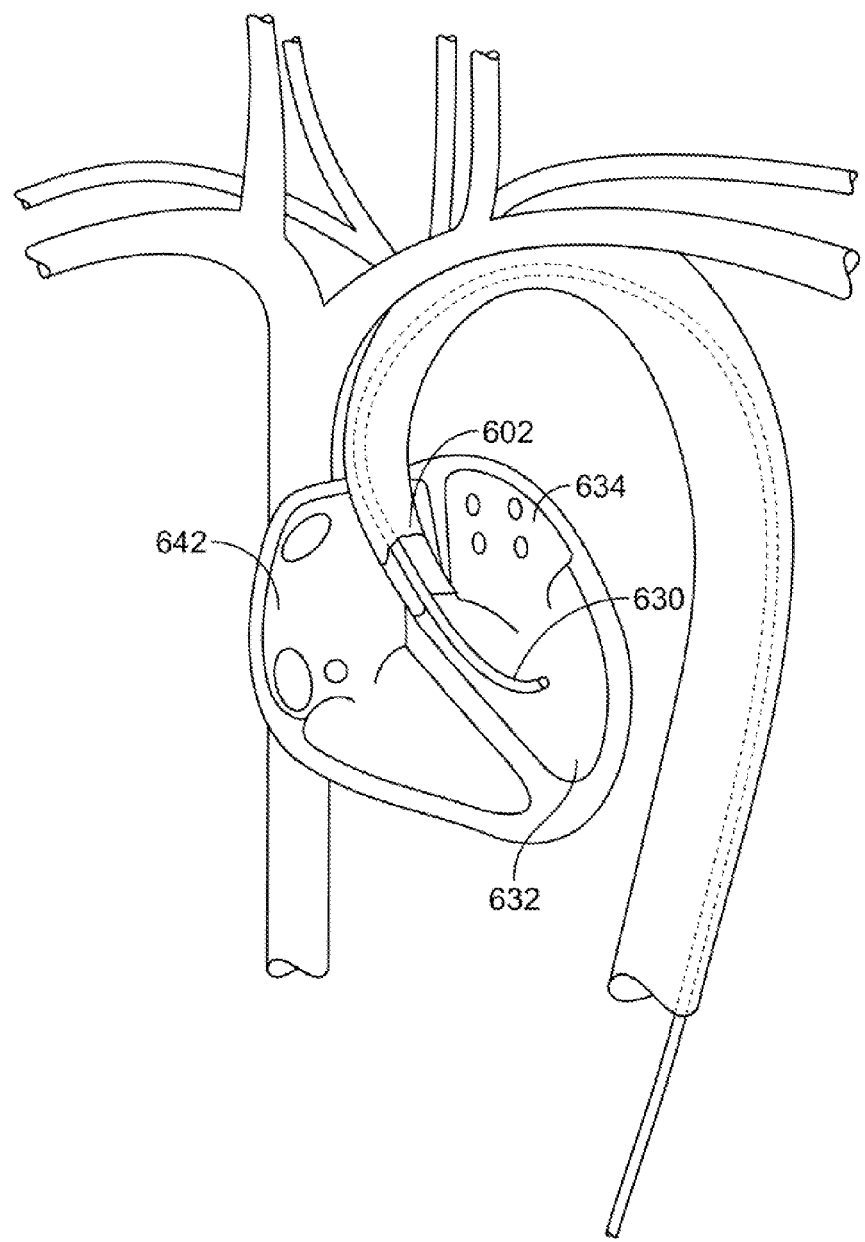
Figure 16C:
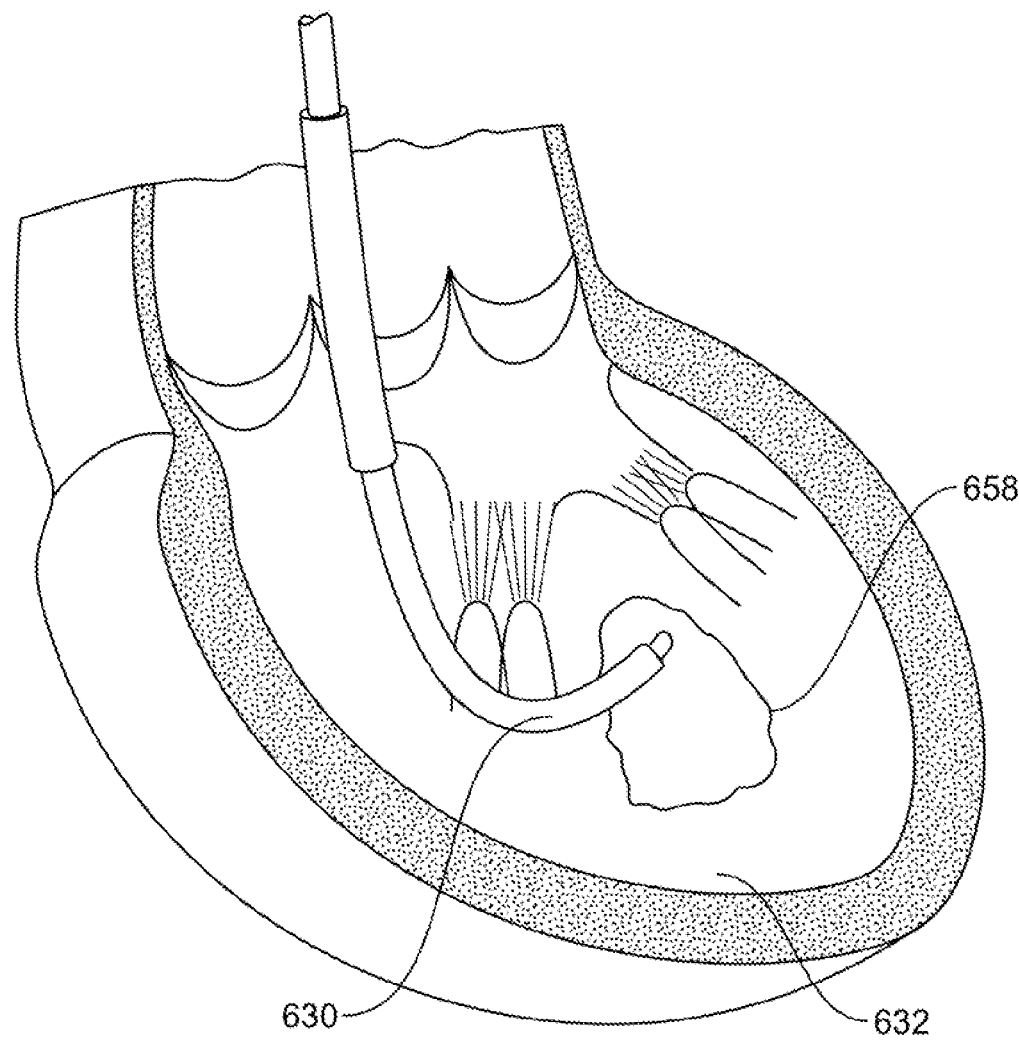
Figure 16D:
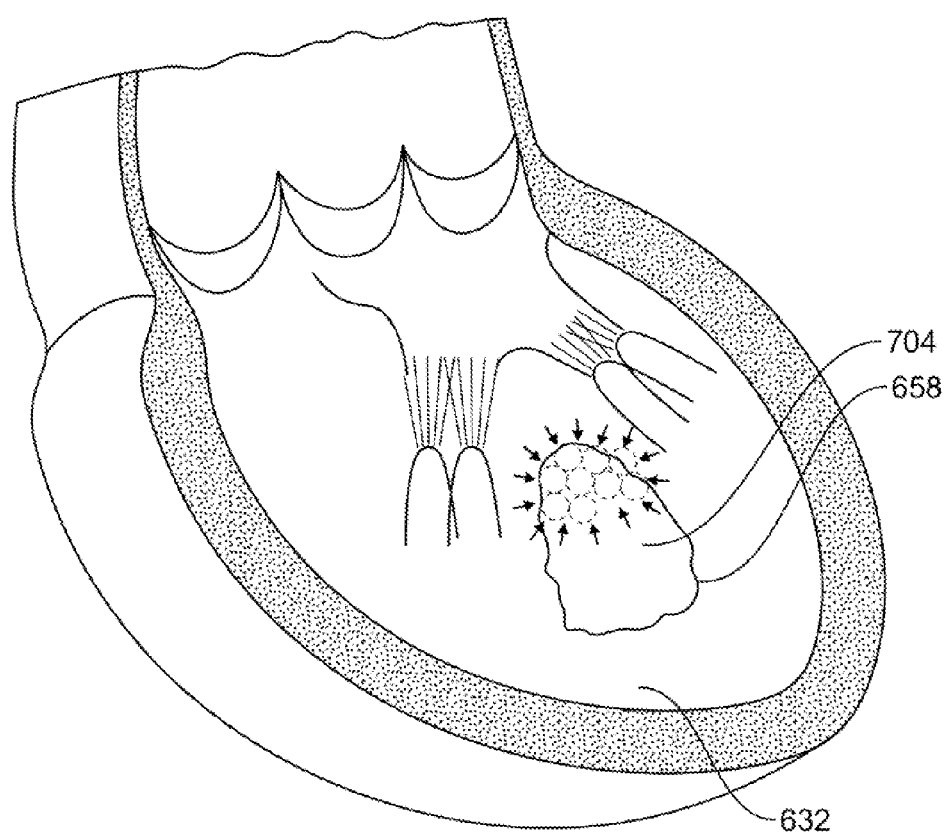
Figure 16E:
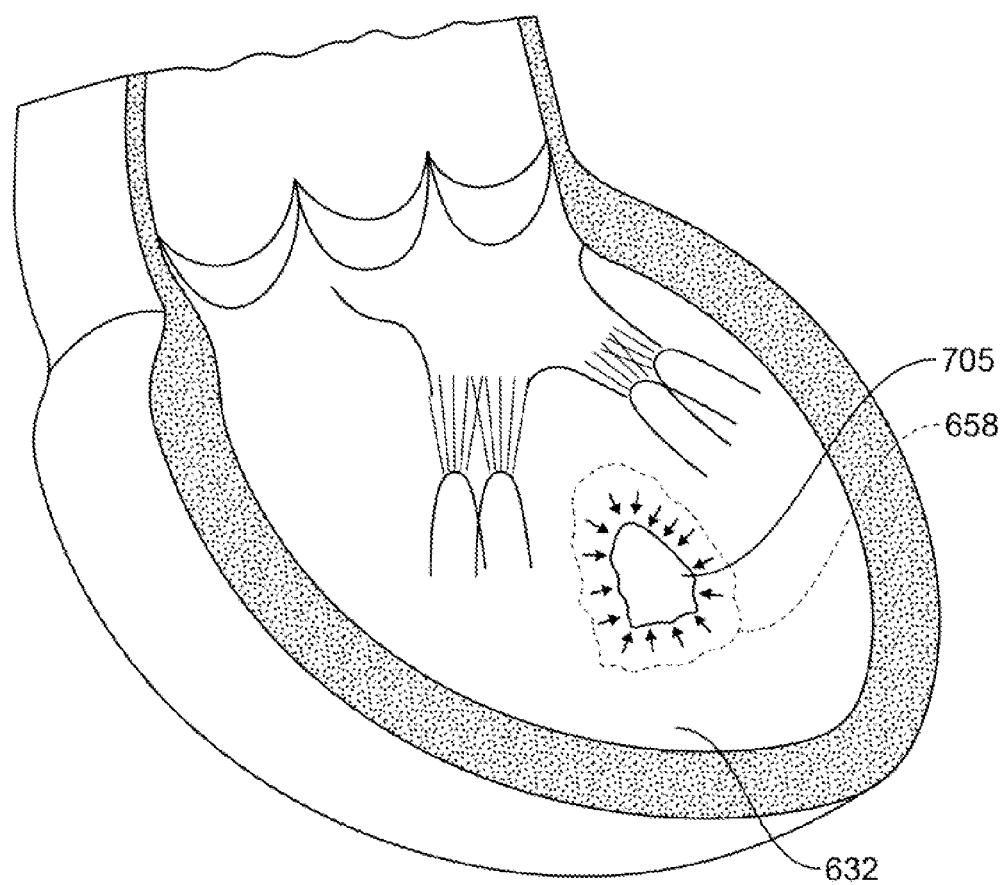
Figure 16F:
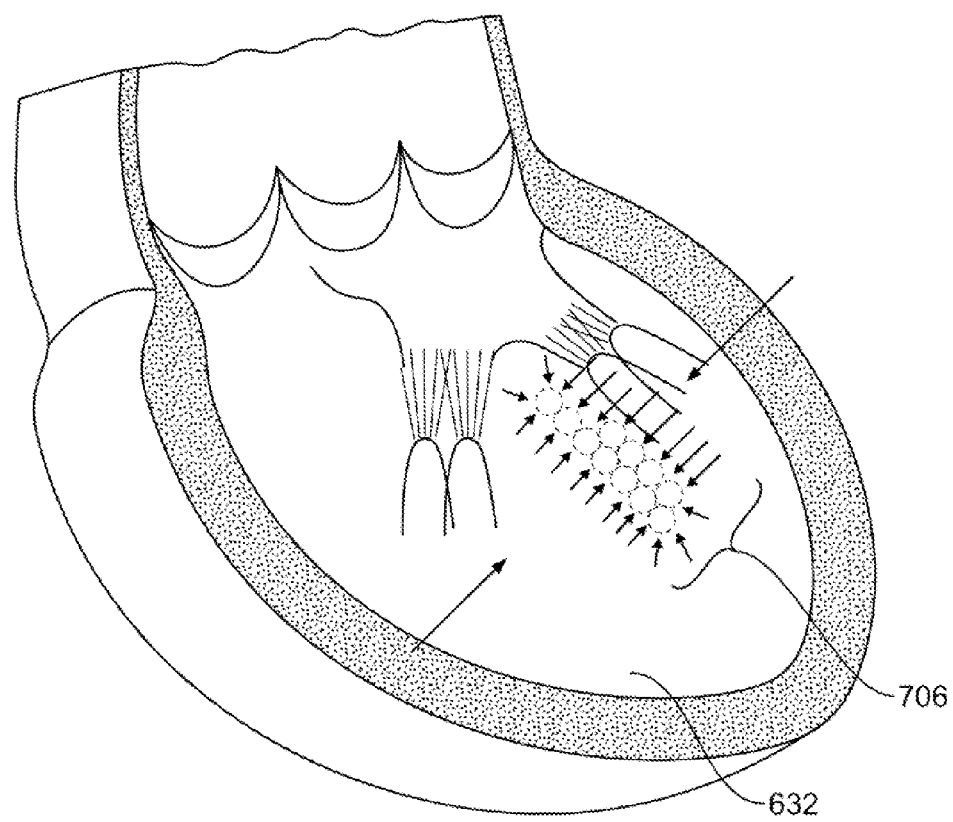

Referring to FIGS. 16A-F, a system similar to that described in reference to the denaturation/fixation processes for addressing mitral valve disease by directly modifying and fixing the geometry of the mitral valve tissue may be utilized to address localized deformation due to infarction, and thereby address associated mitral valve and/or left ventricular problems. Referring to FIG. 16A, a very typical position of a myocardial infarction is depicted. An initial infarcted area is depicted (656), along with a post-infarct expansion area (658) into which the infarct generally may spread. Due to the localized stretching or spreading and tissue mechanics change associated with an infarction, along with the generally poor contractility of the infracted area, the heart may ultimately have a decreased injection fraction and increased left ventricular volume. To address this, a steerable elongate instrument with a distal tip configured to locally and precisely denature the collagenous tissue of the infarcted and noninfarcted myocardium, and/or fix the denatured tissue with a chemical fixative such as genepin, may be utilized. Such a system may be delivered to the left ventricle (632) through an arterial approach through the aortic valve (602), as depicted in FIG. 16B. FIG. 16C depicts the distal tip of the instrument (630) steering over to the targeted tissue surface and touching a localized target area where it may be used to induce a localized denaturation, preferably along with a localized injection of a fixative agent such as genepin, utilizing a probe distal tip such as those described in reference to FIGS. 11A-H. The shape of the post-infarct expansion area (658) is depicted. FIG. 16D depicts how a field (704) of closely related localized target areas for shrinkage and fixation treatment may be utilized to produce a net effect of shrinking an infarcted area to a minimized geometry (705), as depicted in FIG. 16E, wherein the net infarcted area after the treatment (705) is decreased from the original area of the infarct before the procedure. Referring to FIG. 16F, one or more linear series of localized denaturations and/or fixations (706) may be utilized to tune the relative positioning of the papillary complexes with or without the presence of an infarct. Myocardial tuning like this may be known as "left ventricular remodeling", and conventionally involves a series of imbrications generally formed with sutures in a substantially invasive and dangerous procedure. The subject catheter-based procedure provides a minimally invasive option.

Figure 17A:
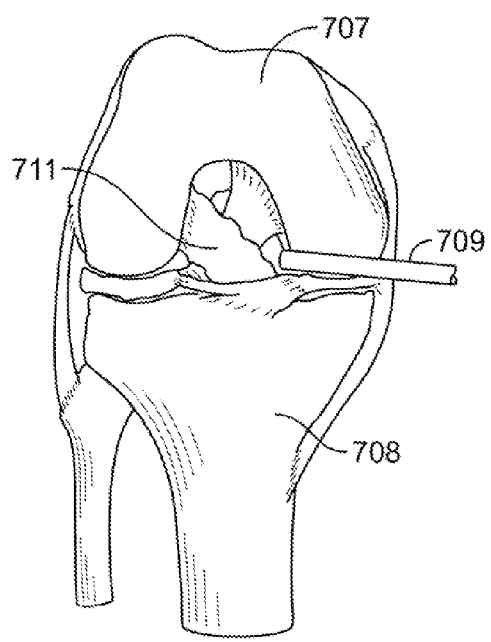
FIGS. 17A-18D show various systems for treating various tissues.
Figure 17B:
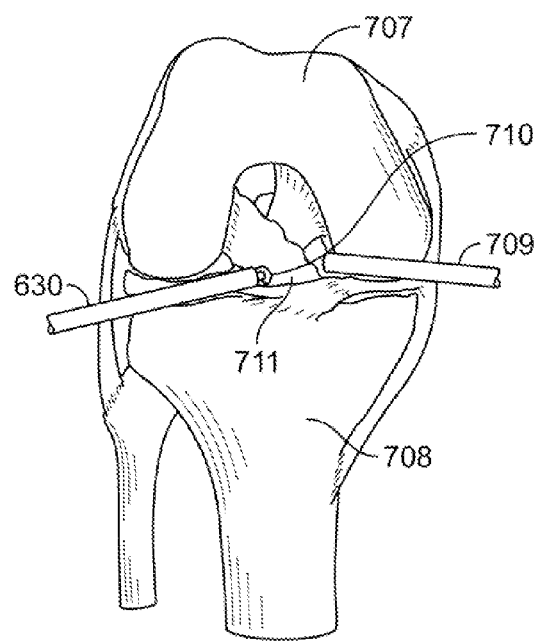
Figure 17C:
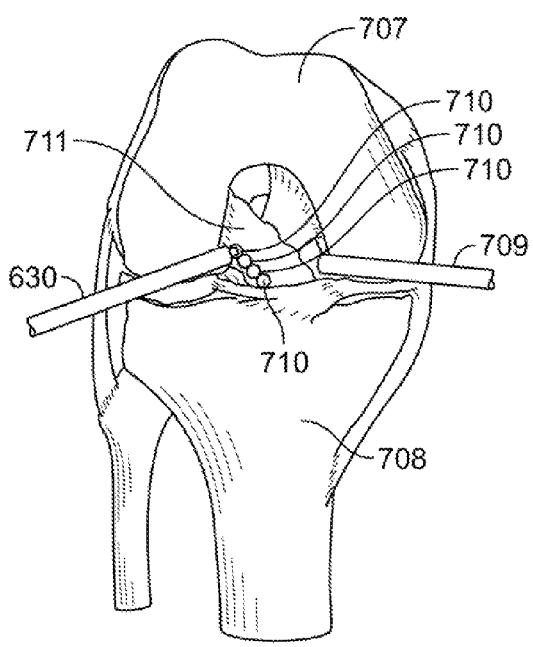
Figure 17D:
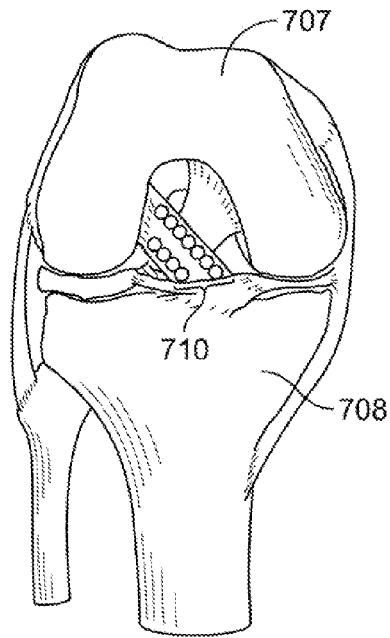
Figure 18A:
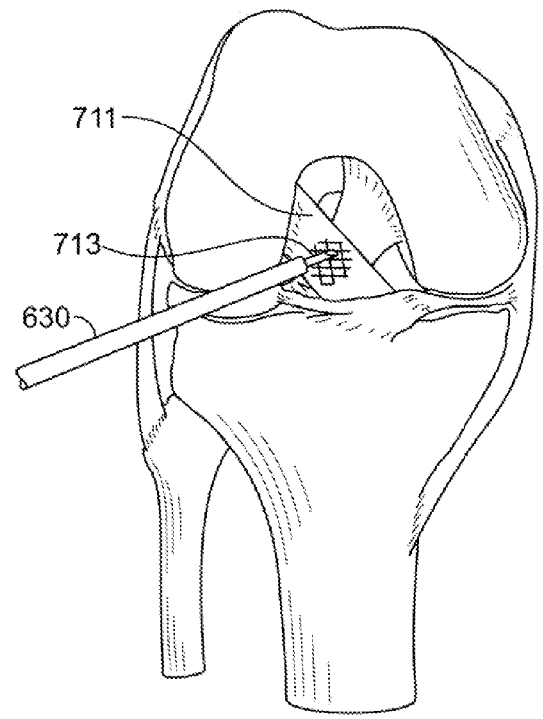
Figure 18B:
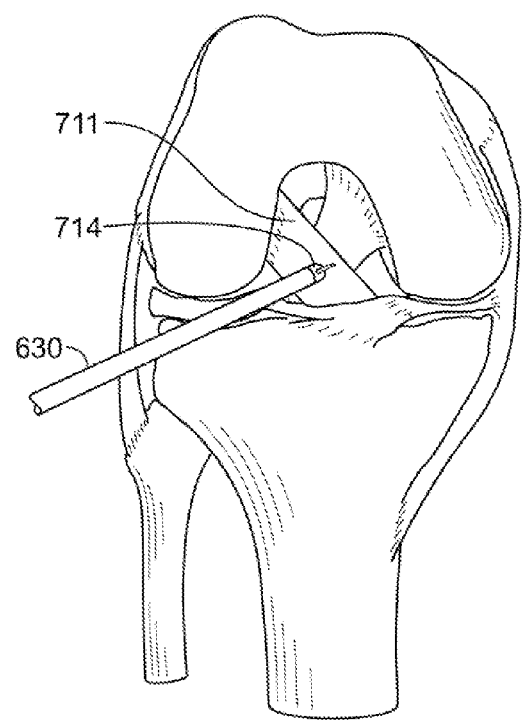
Figure 18C:
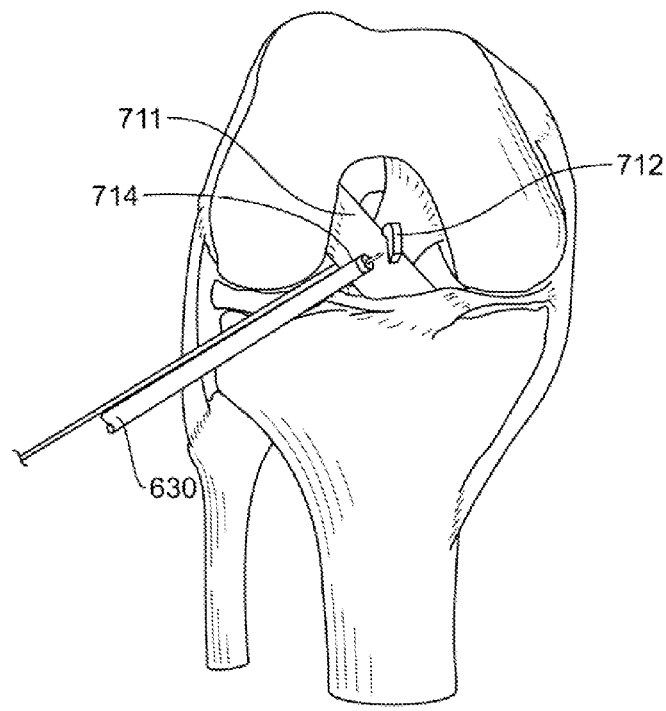
Figure 18D:
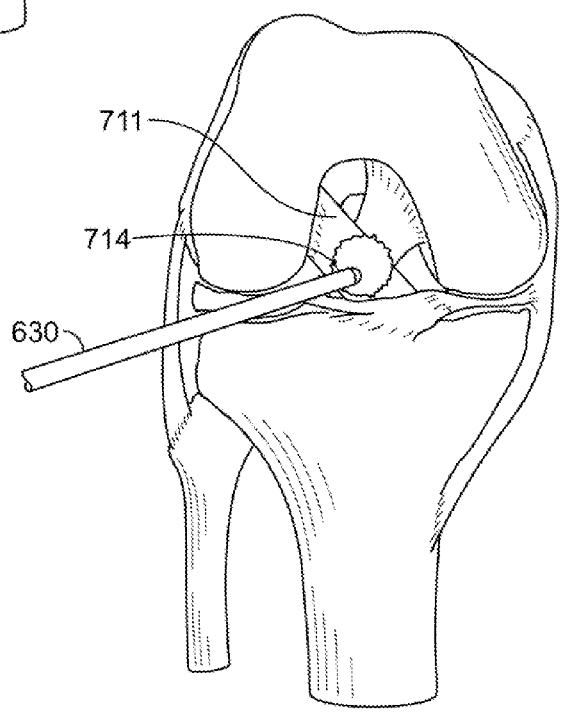

Referring to FIGS. 17A-18D, the inventive systems and techniques may be utilized to address other collagenous tissue interventions. For example, as depicted in FIGS. 17A-D, an arthroscope (709) and treatment probe (630) with a distal tip configured to denature and/or chemically fix collagenous tissue may be utilized to controllably shrink and/or fix a lax anterior cruciate ligament (711), positioned between the femur (707) and tibia (708) of the human knee. As depicted in FIG. 17A, a conventional arthroscope (709) may be introduced with conventional port access and saline-flushing technique. As depicted in FIG. 17B, a treatment probe (630) may be introduced as well, through a different port, to enable the operator to controllably contact the anterior cruciate ligament tissue and create lesions (710) in a desired pattern. In another embodiment, an arthroscope camera device may comprise the same minimally invasive elongate mechanical platform as the treatment probe, thus requiring only one surgical access port. Referring to FIG. 17C, a long linear lesion is created from a line of smaller lesions (711) to create an asymmetric tightening of the ligament along the vector of the linear lesion. Referring to FIG. 17D, two long linear lesions are created from lines of smaller lesions (710) to provide a more symmetric tightening of the ligament. Many distal tips may be utilized to create lesions within ligamentous tissue. For example, referring to FIG. 18A, a probe (630) comprising a needle tip may be utilized to create a deeper lesion within the ligament (711). Referring to FIG. 18B, a needle/electrode tip (714) may be utilized to denature and/or inject fixative precisely into the ligament (711). Referring to FIG. 18C, a probe embodiment similar to that depicted in FIG. 18B is depicted, with the exception that the embodiment of FIG. 18C also comprises a mechanical protrusion limiter structure (712) which may be placed around the opposite side of the subject ligament (711) to ensure that a needle protrusion to the limits of the limiter structure (712) crosses the entire ligament and not other tissue. Referring to FIG. 18D, a needle-less tip may be utilized for needle-less chemical fixative injection, topical fixative administration, and/or denaturing with an associated electrode.

While multiple embodiments and variations of the many aspects of the invention have been disclosed and described herein, such disclosure is provided for purposes of illustration only.

What is claim:

1. A method for modifying a valve in a subject's body, comprising:
   endoluminally advancing an elongate flexible instrument to within a vicinity of a valve in a subject's body;
   heating a tissue mass located in a vicinity of the valve to a temperature sufficient to shrink the tissue mass, thereby modifying the shape or position of a valve to modify flow through the valve; and
   introducing a biocompatible fixative into the tissue mass after heating the tissue mass, to retain shrinkage or tightening of the tissue mass and to retain the modified shape or position of the valve.

2. The method of claim 1, wherein the tissue mass is heated using radio frequency energy.

3. The method of claim 1, wherein the fixative is introduced into the tissue mass by injection.

4. The method of claim 1, wherein the tissue mass is heated using radio frequency energy delivered using an electrode carried on a flexible catheter, and wherein the fixative is inserted into the tissue mass by injection with a needle carried by the flexible catheter.

5. The method of claim 4, wherein the needle comprises the electrode.

6. The method of claim 4, wherein the flexible catheter is robotically controlled.

7. The method of claim 6, wherein the catheter is actuated by an instrument driver in response to signals generated by manipulation of a controller.

8. The method of claim 6, wherein the needle is controllably retractable and advanceable out of a port of the flexible catheter.

9. The method of claim 8, the flexible catheter comprising an imaging device having a field of view, the imaging device oriented such that at least a portion of the needle, when advanced out of the catheter port, is captured within the field of view.

10. The method of claim 9, the imaging device comprising an ultrasound transducer.

11. The method of claim 9, the imaging device comprising a CCD or optical camera.

12. The method of claim 1, wherein the fixative comprises genepin.

13. The method of claim 1, wherein endoluminally advancing an elongate flexible instrument comprises intravascularly advancing an elongate flexible instrument.

14. The method of claim 1, wherein the tissue mass is a biological valve annulus.

15. The method of claim 14, wherein modifying the shape or position of a valve comprises modifying valve coaptation.

16. The method of claim 1, wherein modifying the shape or position of a valve comprises modifying the shape or position of a valve annulus, valve leaflet or chordae tendineae.

* * * * *